(12) United States Patent
Dunne

(10) Patent No.: US 12,128,034 B2
(45) Date of Patent: Oct. 29, 2024

(54) COMBINATIONS OF BETA-LACTAM COMPOUNDS, PROBENECID, AND VALPROIC ACID AND USES THEREOF

(71) Applicant: Iterum Therapeutics International Limited, Dublin (IE)

(72) Inventor: Michael Dunne, Old Saybrook, CT (US)

(73) Assignee: Iterum Therapeutics International Limited, Dublin (IE)

(*) Notice: Subject to any disclaimer, the term of this patent is extended or adjusted under 35 U.S.C. 154(b) by 312 days.

(21) Appl. No.: 17/198,335

(22) Filed: Mar. 11, 2021

(65) Prior Publication Data

US 2021/0283112 A1  Sep. 16, 2021

Related U.S. Application Data

(60) Provisional application No. 62/987,963, filed on Mar. 11, 2020.

(51) Int. Cl.
| | | |
|---|---|---|
| A61K 31/431 | (2006.01) | |
| A61K 9/00 | (2006.01) | |
| A61K 9/20 | (2006.01) | |
| A61K 31/18 | (2006.01) | |
| A61K 31/19 | (2006.01) | |

(52) U.S. Cl.
CPC .......... *A61K 31/431* (2013.01); *A61K 9/0019* (2013.01); *A61K 9/0053* (2013.01); *A61K 9/2086* (2013.01); *A61K 31/18* (2013.01); *A61K 31/19* (2013.01)

(58) Field of Classification Search
CPC .... A61K 2300/00; A61K 31/18; A61K 31/19; A61K 31/245; A61K 31/431; A61K 9/0019; A61K 9/0053; A61K 9/2086; A61P 25/08; A61P 31/04
See application file for complete search history.

(56) References Cited

U.S. PATENT DOCUMENTS

2019/0374516 A1* 12/2019 Dunne .................. A61K 47/26

FOREIGN PATENT DOCUMENTS

| CN | 102014957 A | 4/2011 |
|---|---|---|
| WO | WO-2019012109 A1 | 1/2019 |

OTHER PUBLICATIONS

Horiuchi et al ( Toxicology, 222 (2006) 114-124)., (Year: 2006).*
Deshayes et al (Drug Saf (2017, 40:1171-1198) (Year: 2017).*
Zhang et al. (Bioscience hypotheses (2009) 2, 316-318) (Year: 2009).*
Pony Yee-Chee et al. (Expert opinion on drug safety, 2021, vol. 20, No. 2, 215-223) (Year: 2021).*

(Continued)

*Primary Examiner* — Savitha M Rao
(74) *Attorney, Agent, or Firm* — COOLEY LLP

(57) ABSTRACT

The present disclosure relates to combinations of valproic acid or a pharmaceutically acceptable salt thereof, a β-lactam compound or a pharmaceutically acceptable salt thereof, and probenecid or a pharmaceutically acceptable salt thereof. The present disclosure also relates to methods of treating or preventing a disease using the combinations.

16 Claims, 3 Drawing Sheets

(56) References Cited

OTHER PUBLICATIONS

Dacey, R. G. & Sande, M. E., "Effect of Probenecid on Cerebrospinal Fluid Concentrations of Penicillin and Cephalosporin Derivatives," Antimicrobial Agents and Chemotherapy, 6(4):437-441 (1974).

Dominy, S. S. et al., "*Porphyromonas gingivalis* in Alzheimer's disease brains: Evidence for disease causation and treatment with small-molecule inhibitors," Sci. Adv. 5:eaau3333 (2019); doi:10.1126/sciadv.aau3333, 21 pages.

Ednie, L. M. & Applebaum, P. C., "Antianaerobic Activity of Sulopenem Compared to Six Other Agents," Antimicrobial Agents and Chemotherapy, 53(5):2163-2170 (2009).

Al-Quteimat, O. & Laila, A., "Valproate Interaction With Carbapenems: Review and Recommendations," Hospital Pharmacy, 55(3):182-188 (2020).

Park, M. K. et al., "Reduced Valproic Acid Serum Concentrations Due to Drug Interactions With Carbapenem Antibiotics: Overview of 6 Cases," Ther Drug Monit, 34:599-603 (2012).

Huang, C., et al., "Drug interaction between valproic acid and carbapenems in patients with epileptic seizures," The Kaohsiung Journal of Medical Sciences, 2017, vol. 33(3), pp. 130-136.

Schafer, S. et al., "Failure is an option: learning from unsuccessful proof-of-concept trials," Drug Discov. Today., Nov. 2008; 13(21-22): 913-916.

Zhang, X.-h et al., "Effects of probenecid on the intestinal absorption of cefaclor in rats," Chinese Journal of Clinical Pharmacology and Therapeutics, 12:1344-1349 (2008).

Zhanqing, W., et al., "Advances in the Study of Probenecid in Combination with Other Drugs", Chinese Journal of Pharmacology, 40(21):1607-1609 (2005), w/English translation, 9 pages.

\* cited by examiner

COMBINATIONS OF BETA-LACTAM COMPOUNDS, PROBENECID, AND VALPROIC ACID AND USES THEREOF

RELATED APPLICATIONS

This application claims the benefit of and priority to U.S. provisional application No. 62/987,963, filed Mar. 11, 2020, the entire contents of which are incorporated herein by reference in its entirety.

BACKGROUND

β-lactam compounds are a class of antibiotics having a beta-lactam ring in their molecular structures. β-lactam compounds have been used in the treatment of diseases associated with Gram-positive and Gram-negative bacteria. Valproic acid ("VPA") is a medication used primarily for the treatment of patients with seizure disorders and less frequently for other nervous system disorders such as mania and migroane headaches. Coadministration of valproic acid and a β-lactam compound, including a penem class antibiotic, may be necessary for treatment of an acute infection. A clinically significant reduction in serum valproic acid concentration has been reported in patients receiving carbapenem antibiotics (for example, ertapenem, imipenem, and meropenem, among others) and may result in loss of seizure control. The mechanism of this interaction is not well understood.

SUMMARY

In some aspects, the present disclosure provides a method of treating or preventing a disease, comprising administering to a subject in need thereof:
  a pharmaceutically effective amount of valproic acid or a pharmaceutically acceptable salt thereof;
  a pharmaceutically effective amount of a β-lactam compound or a pharmaceutically acceptable salt thereof, and
  a pharmaceutically effective amount of probenecid or a pharmaceutically acceptable salt thereof.

In some aspects, the present disclosure provides a method of treating or preventing a disease in a subject being administered with valproic acid or a pharmaceutically acceptable salt thereof, comprising administering to a subject in need thereof:
  a pharmaceutically effective amount of a β-lactam compound or a pharmaceutically acceptable salt thereof, and
  a pharmaceutically effective amount of probenecid or a pharmaceutically acceptable salt thereof.

In some aspects, the present disclosure provides a method of treating or preventing a disease in a subject being administered with valproic acid or a pharmaceutically acceptable salt thereof and a β-lactam compound or a pharmaceutically acceptable salt thereof, comprising administering to a subject in need thereof:
  a pharmaceutically effective amount of probenecid or a pharmaceutically acceptable salt thereof.

In some aspects, the present disclosure provides a method of reducing or alleviating a side effect in a subject being administered with valproic acid or a pharmaceutically acceptable salt thereof and a β-lactam compound or a pharmaceutically acceptable salt thereof, comprising administering to a subject in need thereof:
  a pharmaceutically effective amount of probenecid or a pharmaceutically acceptable salt thereof.

In some aspects, the present disclosure provides a combination for treating or preventing a disease, wherein the combination comprises:
  a pharmaceutically effective amount of valproic acid or a pharmaceutically acceptable salt thereof;
  a pharmaceutically effective amount of a β-lactam compound or a pharmaceutically acceptable salt thereof, and
  a pharmaceutically effective amount of probenecid or a pharmaceutically acceptable salt thereof.

In some aspects, the present disclosure provides a combination for treating or preventing a disease in a subject being administered valproic acid or a pharmaceutically acceptable salt thereof, wherein the combination comprises:
  a pharmaceutically effective amount of a β-lactam compound or a pharmaceutically acceptable salt thereof, and
  a pharmaceutically effective amount of probenecid or a pharmaceutically acceptable salt thereof.

In some aspects, the present disclosure provides probenecid or a pharmaceutically acceptable salt thereof for treating or preventing a disease in a subject being administered valproic acid or a pharmaceutically acceptable salt thereof and a β-lactam compound or a pharmaceutically acceptable salt thereof.

In some aspects, the present disclosure provides probenecid or a pharmaceutically acceptable salt thereof for reducing or alleviating a side effect in a subject being administered valproic acid or a pharmaceutically acceptable salt thereof and a β-lactam compound or a pharmaceutically acceptable salt thereof.

In some aspects, the present disclosure provides a combination comprising:
  a pharmaceutically effective amount of valproic acid or a pharmaceutically acceptable salt thereof;
  a pharmaceutically effective amount of a β-lactam compound or a pharmaceutically acceptable salt thereof, and
  a pharmaceutically effective amount of probenecid or a pharmaceutically acceptable salt thereof.

In some aspects, the present disclosure provides a pharmaceutical kit comprising:
  a pharmaceutically effective amount of valproic acid or a pharmaceutically acceptable salt thereof;
  a pharmaceutically effective amount of a β-lactam compound or a pharmaceutically acceptable salt thereof, and
  a pharmaceutically effective amount of probenecid or a pharmaceutically acceptable salt thereof.

In some aspects, the present disclosure provides a pharmaceutical composition comprising:
  a pharmaceutically effective amount of valproic acid or a pharmaceutically acceptable salt thereof;
  a pharmaceutically effective amount of a β-lactam compound or a pharmaceutically acceptable salt thereof, and
  a pharmaceutically effective amount of probenecid or a pharmaceutically acceptable salt thereof.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

DETAILED DESCRIPTION

Figure 1:
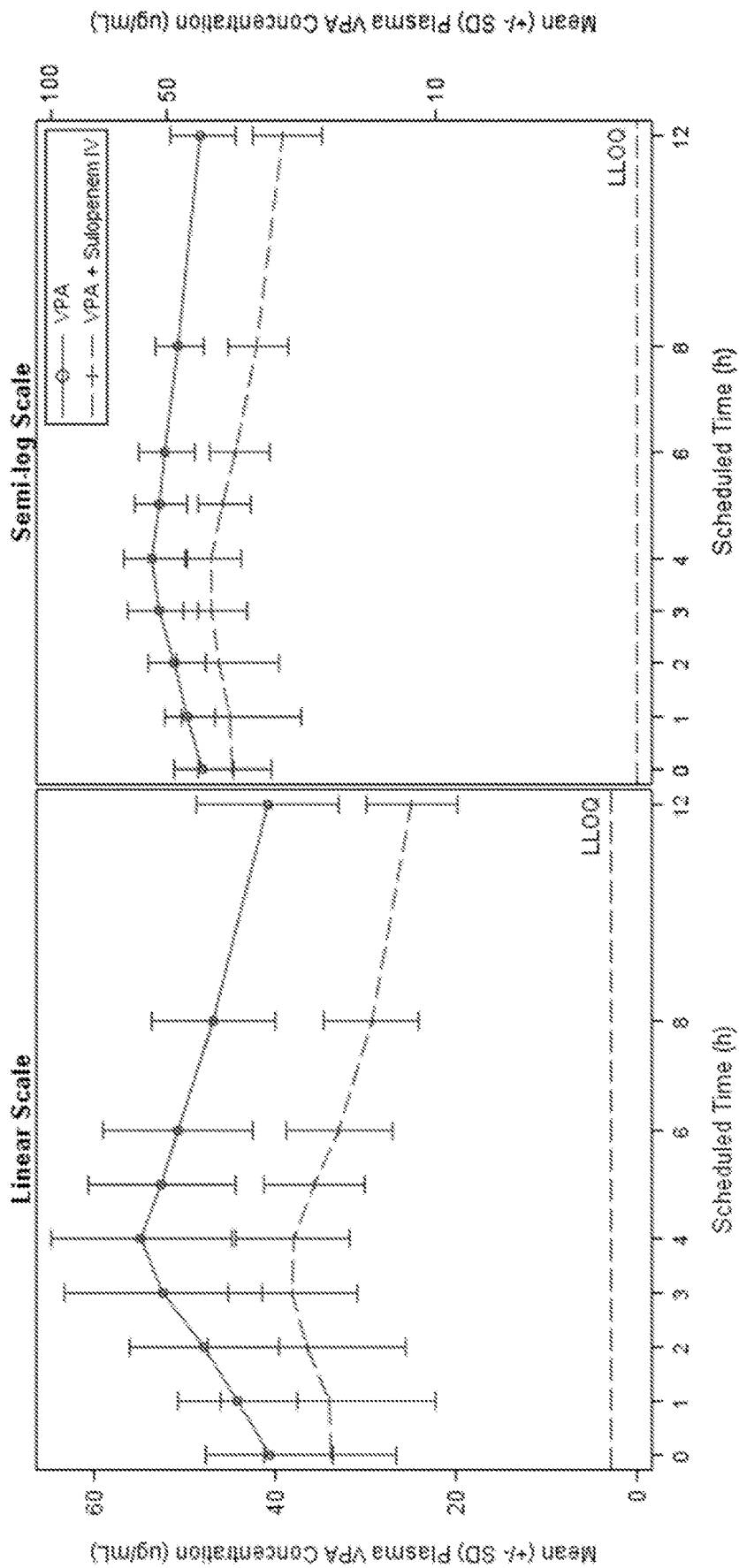
FIG. 1 is a diagram showing the mean (±standard deviation) plasma concentration of valproic acid (µg/ml) when being administered alone and in combination with sulopenem (in intravenous formulation).

In some aspects, the present disclosure provides a method of treating or preventing a disease, comprising administering to a subject in need thereof:
 a pharmaceutically effective amount of valproic acid or a pharmaceutically acceptable salt thereof;
 a pharmaceutically effective amount of a β-lactam compound or a pharmaceutically acceptable salt thereof, and
 a pharmaceutically effective amount of probenecid or a pharmaceutically acceptable salt thereof.

In some aspects, the present disclosure provides a method of treating or preventing a disease in a subject being administered with valproic acid or a pharmaceutically acceptable salt thereof, comprising administering to a subject in need thereof:
 a pharmaceutically effective amount of a β-lactam compound or a pharmaceutically acceptable salt thereof, and
 a pharmaceutically effective amount of probenecid or a pharmaceutically acceptable salt thereof.

In some aspects, the present disclosure provides a method of treating or preventing a disease in a subject being administered valproic acid or a pharmaceutically acceptable salt thereof and a β-lactam compound or a pharmaceutically acceptable salt thereof, comprising administering to a subject in need thereof:
 a pharmaceutically effective amount of probenecid or a pharmaceutically acceptable salt thereof.

In some aspects, the present disclosure provides a method of reducing or alleviating a side effect in a subject being administered with valproic acid or a pharmaceutically acceptable salt thereof and a β-lactam compound or a pharmaceutically acceptable salt thereof, comprising administering to a subject in need thereof:
 a pharmaceutically effective amount of probenecid or a pharmaceutically acceptable salt thereof.

In some aspects, the present disclosure provides a combination for treating or preventing a disease, wherein the combination comprises:
 a pharmaceutically effective amount of valproic acid or a pharmaceutically acceptable salt thereof;
 a pharmaceutically effective amount of a β-lactam compound or a pharmaceutically acceptable salt thereof, and
 a pharmaceutically effective amount of probenecid or a pharmaceutically acceptable salt thereof.

In some aspects, the present disclosure provides a combination for treating or preventing a disease in a subject being administered valproic acid or a pharmaceutically acceptable salt thereof, wherein the combination comprises:
 a pharmaceutically effective amount of a β-lactam compound or a pharmaceutically acceptable salt thereof, and
 a pharmaceutically effective amount of probenecid or a pharmaceutically acceptable salt thereof.

In some aspects, the present disclosure provides probenecid or a pharmaceutically acceptable salt thereof for treating or preventing a disease in a subject being administered with valproic acid or a pharmaceutically acceptable salt thereof and a β-lactam compound or a pharmaceutically acceptable salt thereof.

In some aspects, the present disclosure provides probenecid or a pharmaceutically acceptable salt thereof for reducing or alleviating a side effect in a subject being administered with valproic acid or a pharmaceutically acceptable salt thereof and a β-lactam compound or a pharmaceutically acceptable salt thereof.

Effects of the Methods

In some embodiments, the administration reduces or alleviates a side effect.

In some embodiments, the administration reduces or alleviates a side effect of administering valproic acid or a pharmaceutically acceptable salt thereof and a β-lactam compound or a pharmaceutically acceptable salt thereof without administering probenecid or the pharmaceutically acceptable salt thereof.

In some embodiments, the side effect is mania, a seizure, an increased seizure potential, a reduced concentration of valproic acid in the subject, neuromotor impairment, or a potential for neuromotor impairment.

In some embodiments, the side effect is mania.

In some embodiments, the side effect is mania associated with bipolar disease and/or migraine.

In some embodiments, the side effect is a seizure.

In some embodiments, the side effect is an increased seizure potential.

In some embodiments, the side effect is a reduced concentration of valproic acid in the subject.

In some embodiments, the side effect is neuromotor impairment.

In some embodiments, the side effect is a potential for neuromotor impairment.

In some embodiments, the side effect is a seizure associated with the administration of a β-lactam compound.

In some embodiments, the side effect is a seizure associated with the co-administration of a β-lactam compound and valproic acid.

In some embodiments, the side effect is an increased seizure potential associated with the administration of a β-lactam compound.

In some embodiments, the side effect is an increased seizure potential associated with the co-administration of a β-lactam compound and valproic acid.

In some embodiments, the side effect is a reduced concentration of valproic acid in the subject associated with the co-administration of a β-lactam compound. In some embodiments, the side effect is neuromotor impairment associated with the administration of a β-lactam compound.

In some embodiments, the side effect is neuromotor impairment associated with the co-administration of a β-lactam compound and valproic acid.

In some embodiments, the side effect is a potential for neuromotor impairment associated with the administration of a β-lactam compound.

In some embodiments, the side effect is a potential for neuromotor impairment associated with the co-administration of a β-lactam compound and valproic acid.

In some embodiments, the administration results in a lower seizure potential in the subject as compared to a comparable subject being administered without probenecid or the pharmaceutically acceptable salt thereof.

In some embodiments, the administration results in an increased concentration of valproic acid in the subject as compared to a comparable subject being administered without probenecid or the pharmaceutically acceptable salt thereof.

In some embodiments, the administration results in a lower potential for neuromotor impairment in the subject as compared to a comparable subject being administered without probenecid or the pharmaceutically acceptable salt thereof.

In some embodiments, the administration results in a plasma concentration for the valproic acid or pharmaceutically acceptable salt thereof having an area under the curve (AUC) that is higher in the subject in need thereof as compared to a comparable subject being administered with the β-lactam compound or pharmaceutically acceptable salt thereof and valproic acid or pharmaceutically acceptable salt thereof without probenecid or pharmaceutically acceptable salt thereof within about 15 minutes, about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration.

In some embodiments, the administration results in a plasma concentration for the valproic acid or pharmaceutically acceptable salt thereof having an area under the curve (AUC) that is higher in the subject in need thereof as compared to a comparable subject being administered with the β-lactam compound or pharmaceutically acceptable salt thereof and valproic acid or pharmaceutically acceptable salt thereof without probenecid or pharmaceutically acceptable salt thereof by about 0.1% or greater, about 0.25% or greater, about 0.5% or greater, about 0.75% or greater, about 1% or greater, about 2% or greater, about 3% or greater, about 4% or greater, about 5% or greater, about 6% or greater, about 7% or greater, about 8% or greater, about 9% or greater, about 10% or greater, about 15% or greater, about 20% or greater, about 25% or greater, about 30% or greater, about 40% or greater, about 50% or greater, about 60% or greater, about 80% or greater, about 100% or greater, about 150% or greater, about 200% or greater, about 300% or greater, about 400% or greater, or about 500% or greater within about 15 minutes, about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration.

In some embodiments, the administration results in a plasma concentration for the valproic acid or pharmaceutically acceptable salt thereof having a maximum plasma concentration ($C_{max}$) that is higher in the subject in need thereof as compared to a comparable subject being administered with the β-lactam compound or pharmaceutically acceptable salt thereof and valproic acid or pharmaceutically acceptable salt thereof without probenecid or pharmaceutically acceptable salt thereof within about 15 minutes, about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration.

In some embodiments, the administration results in a plasma concentration for the valproic acid or pharmaceutically acceptable salt thereof having a maximum plasma concentration ($C_{max}$) that is higher in the subject in need thereof as compared to a comparable subject being administered with the β-lactam compound or pharmaceutically acceptable salt thereof and valproic acid or pharmaceutically acceptable salt thereof without probenecid or pharmaceutically acceptable salt thereof by about 0.1% or greater, about 0.25% or greater, about 0.5% or greater, about 0.75% or greater, about 1% or greater, about 2% or greater, about 3% or greater, about 4% or greater, about 5% or greater, about 6% or greater, about 7% or greater, about 8% or greater, about 9% or greater, about 10% or greater, about 15% or greater, about 20% or greater, about 25% or greater, about 30% or greater, about 40% or greater, about 50% or greater, about 60% or greater, about 80% or greater, about 100% or greater, about 150% or greater, about 200% or greater, about 300% or greater, about 400% or greater, or about 500% or greater within about 15 minutes, about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration.

In some embodiments, administration results in a plasma concentration for valproic acid or pharmaceutically acceptable salt thereof having an area under the curve (AUC) in the subject in need thereof that is substantially the same as compared to a comparable subject being administered with valproic acid or pharmaceutically acceptable salt thereof without the β-lactam compound, probenecid, or the pharmaceutically acceptable salt thereof within about 15 minutes, about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration.

In some embodiments, the administration results in a plasma concentration for valproic acid or pharmaceutically acceptable salt thereof having an area under the curve (AUC) in the subject in need thereof that ranges from about 50% to about 150%, from about 60% to about 140%, from about 70% to about 130%, from about 80% to about 120%, from about 90% to about 110%, or from about 95% to about 105% of the area under the curve (AUC) resulted in a comparable subject being administered with valproic acid or pharmaceutically acceptable salt thereof without the β-lactam compound, probenecid, or the or pharmaceutically acceptable salt thereof within about 15 minutes, about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration.

In some embodiments, the administration results in a plasma concentration for valproic acid or pharmaceutically acceptable salt thereof having an area under the curve (AUC) in the subject in need thereof that is about 50%, about 60%, about 70%, about 80%, about 90%, about 95%, about 98%, about 102%, about 105%, about 110%, about 115%, about 120%, about 125%, about 130%, about 140%, or about 150% of the area under the curve (AUC) resulted in a comparable subject being administered with valproic acid or pharmaceutically acceptable salt thereof without the β-lactam compound, probenecid, or pharmaceutically acceptable salt thereof within about 15 minutes, about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration.

In some embodiments, administration results in a plasma concentration for valproic acid or pharmaceutically acceptable salt thereof having a maximum plasma concentration ($C_{max}$) in the subject in need thereof that is substantially the same as compared to a comparable subject being administered with valproic acid or pharmaceutically acceptable salt thereof without the β-lactam compound, probenecid, or the pharmaceutically acceptable salt thereof within about 15 minutes, about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration.

In some embodiments, the administration results in a plasma concentration for valproic acid or pharmaceutically acceptable salt thereof having a maximum plasma concentration ($C_{max}$) in the subject in need thereof that ranges from about 50% to about 150%, from about 60% to about 140%, from about 70% to about 130%, from about 80% to about 120%, from about 90% to about 110%, or from about 95% to about 105% of the maximum plasma concentration ($C_{max}$) resulted in a comparable subject being administered with valproic acid or pharmaceutically acceptable salt thereof without the β-lactam compound, probenecid, or the pharmaceutically acceptable salt thereof within about 15 minutes, about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration.

In some embodiments, the administration results in a plasma concentration for valproic acid or pharmaceutically acceptable salt thereof having a maximum plasma concentration ($C_{max}$) in the subject in need thereof that is about 50%, about 60%, about 70%, about 80%, about 90%, about 95%, about 98%, about 102%, about 105%, about 110%, about 115%, about 120%, about 125%, about 130%, about 140%, or about 150% of the maximum plasma concentration ($C_{max}$) resulted in a comparable subject being administered with valproic acid or pharmaceutically acceptable salt thereof without the β-lactam compound, probenecid, or the pharmaceutically acceptable salt thereof within about 15 minutes, about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration.

Treated Subjects and Diseases

In some embodiments, the subject in need thereof is an animal. In some embodiments, the subject in need thereof is a human.

In some embodiments, the subject in need thereof is a human of 18 years or older.

In some embodiments, the subject in need thereof is a human younger than 18 years.

In some embodiments, the disease is associated with a decreased level of gamma-aminobutyric acid (GABA) in the subject (e.g., in the central nervous system of the subject). In some embodiments, the administration results in an increased level of gamma-aminobutyric acid (GABA) in the subject (e.g., in the central nervous system of the subject).

In some embodiments, the disease is associated with an increased or decreased population of one or more microorganisms (e.g., bacteria) in the subject.

In some embodiments, the disease is associated with an increased population of one or more microorganisms (e.g., bacteria) in the subject. In some embodiments, the administration results in a decrease population of the one or more microorganisms (e.g., bacteria) in the subject.

In some embodiments, the disease is associated with a decreased population of one or more microorganisms (e.g., bacteria) in the subject. In some embodiments, the administration results in an increased population of the one or more microorganisms (e.g., bacteria) in the subject.

In some embodiments, the disease is associated with an increased or decreased population of one or more bacteria selected from *Escherichia coli, Klebsiella pneumoniae, Proteus mirabilis, Enterobacter cloacae, Klebsiella oxytoca, Citrobacter freundii* complex, *Clostridium clostridioforme, Eubacterium lentum, Peptostreptococcus species, Bacteroides fragilis, Bacteroides distasonis, Bacteroides ovatus, Bacteroides thetaiotaomicron, Bacteroides uniformis, Bacteroides coprocola, Prevotella copri, Porphyromonas asaccharolytica,* and *Prevotella bivia* or any organisms in the following genera: *Succinivibrio, Alistipes, Prevotella, Paraprevotella, Parabacteroides,* and *Odoribacter.*

In some embodiments, the disease is associated with an increased or decreased population of one or more bacteria selected from *Staphylococcus epidermidis, Streptococcus pneumonia, Staphylococcus aureus, Streptococcus agalactiae,* and *Streptococcus pyogenes.*

In some embodiments, the disease is associated with an increased or decreased population of one or more bacteria selected from *Citrobacter freundii, Citrobacter koseri, Enterobacter aerogenes, Enterobacter cloacae, Haemophilus influenza, Haemophilus parainfluenzae, Klebsiella oxytoca, Moraxella catarrhalis, Morganella morganii, Proteus vulgaris, Providencia rettgeri, Providencia stuartii,* and *Serratia marcescens.*

In some embodiments, the disease is associated with an increased or decreased population of one or more bacteria selected from *Bacteroides vulgatus, Clostridium perfringens,* and *Fusobacterium* spp.

In some embodiments, the disease is associated with an infection. In some embodiments, the infection is a gram-negative infection. In some embodiments, the infection is a gram-positive infection.

In some embodiments, the infection is resistant to one or more antibiotics when being administered without probenecid or the pharmaceutically acceptable salt thereof.

In some embodiments, the infection is resistant to one or more β-lactam compounds when being administered without probenecid or the pharmaceutically acceptable salt thereof.

In some embodiments, the disease is an uncomplicated urinary tract infection, a complicated urinary tract infection, a complicated intra-abdominal infection, an uncomplicated intra-abdominal infection, pneumonia, otitis media, sinusitis, gonococcal urethritis, pelvic inflammatory disease, prostatitis, bone infection, joint infection, diabetic foot infection and infectious diarrhea.

In some embodiments, the disease is associated with (e.g., resulted from) the alteration of the microbiome in the subject.

In some embodiments, the disease is associated with (e.g., resulted from) the alteration of the microbiome in the human subject.

In some embodiments, the disease is mania.

In some embodiments, the disease is mania associated with bipolar disease and/or migraine.

In some embodiments, the disease is a neurodegenerative disease.

In some embodiments, the disease is amyotrophic lateral sclerosis, Parkinson's disease, Alzheimer's disease, schizophrenia or Huntington's disease.

In some embodiments, the disease is Alzheimer's disease. It is noted that probenecid has been found to increase the concentrations of β-lactam compounds in the cerebrospinal fluid (Ralph G. Dacey and Merle A. Sande, *Antimicrobial Agents and Chemotherapy* 6:437-441 (1974)). More recently, a bacterial pathogen, *Porphyromonas gingivalis*, has been found in brain in association with pathologic lesions, which are associated with Alzheimer's disease (Dominy et al., Sci. Adv. 5:eaau3333 (2019), and sulopenem is active against this bacterium (Lois M. Ednie and Peter C. Appelbaum, *Antimicrobial Agents and Chemotherapy* 53: 2163-2170 (2009)). Without wishing to be bound by theory, it is understood that the β-lactam compounds (e.g., Compound III-2b), when being dosed with probenecid, may lead to more effective treatment of a brain infection with this organism relative to treatment with sulopenem alone.

In some embodiments, the disease is cancer.

In some embodiments, the cancer is a solid cancer, e.g., ovarian cancer, breast cancer, head and neck cancer, renal cancer, bladder cancer, hepatocellular cancer, colorectal cancer, or lymphoma, or any combination thereof.

In some embodiments, the cancer is sarcoma or carcinoma, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, hepatoma, bile duct carcinoma, choriocarcinoma, seminoma, embryonal carcinoma, Wilms' tumor, cervical cancer, testicular tumor, lung carcinoma, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma.

In some embodiments, the cancer is leukemia, e.g., acute lymphocytic leukemia and acute myelocytic leukemia (myeloblastic, promyelocytic, myelomonocytic, monocytic and erythroleukemia); or chronic leukemia (chronic myelocytic (granulocytic) leukemia and chronic lymphocytic leukemia).

In some embodiments, the cancer is polycythemia vera, lymphoma (Hodgkin's disease and non-Hodgkin's disease), multiple myeloma, Waldenstrom's macroglobulinemia, or heavy chain disease.

In some embodiments, the disease is an inflammatory bowel disease.

In some embodiments, the inflammatory bowel disease is Crohn's disease, ulcerative colitis, indeterminate colitis, irritable bowel syndrome, microscopic colitis, deversion colitis, or Behcet's disease.

In some embodiments, the disease is uncomplicated urinary tract infection, complicated urinary tract infection, complicated intra-abdominal infection, acute bacterial prostatitis, community-acquired bacterial pneumonia, gonococcal urethritis, pelvic inflammatory disease, chronic bacterial prostatitis, *Mycobacterium tuberculosis* infection, non-tuberculous mycobacterial infection, bone and joint infection, acute and chronic sinusitis, diabetic foot infection, or infectious diarrhea (e.g., diarrhea caused by *salmonella, shigella*, or *Vibrio cholera*).

β-Lactam Compounds, Probenecid, and Valproic Acid

In some embodiments, the β-lactam compound is a monobactam or a prodrug thereof.

In some embodiments, the β-lactam compound is aztreonam, tigemonam, carumonam, nocardicin A, a prodrug thereof, an analog thereof, or a derivative thereof.

In some embodiments, the β-lactam compound is a penem, a carbapenem, a clavam, or a prodrug thereof.

In some embodiments, the β-lactam compound is benzylpenicillin, benzathine benzylpenicillin, procaine benzylpenicillin, phenoxymethylpenicillin, propicillin, pheneticillin, azidocillin, clometocillin, penamecillin, cloxacillin (e.g., dicloxacillin or flucloxacillin), oxacillin, nafcillin, methicillin, amoxicillin, ampicillin (e.g., pivampicillin, hetacillin, bacampicillin, metampicillin, talampicillin), epicillin, ticarcillin, carbenicillin, carindacillin, temocillin, piperacillin, azlocillin, mezlocillin, mecillinam (e.g., pivmecillinam), sulbenicillin, a pharmaceutically acceptable salt thereof, a prodrug thereof, an analog thereof, or a derivative thereof.

In some embodiments, the β-lactam compound is a penem, a carbapenem, or a prodrug thereof.

In some embodiments, the β-lactam compound a thiopenem, an oxypenem, an aminopenem, an alkylpenems, an arylpenem, or a prodrug thereof.

In some embodiments, the β-lactam compound is ertapenem, an antipseudomonal carbapenem (e.g., doripenem, imipenem, meropenem), biapenem, panipenem, sulopenem, tebipenem, faropenem, a pharmaceutically acceptable salt thereof, a prodrug thereof, an analog thereof, or a derivative thereof.

In some embodiments, the β-lactam compound is a cephem, a carbacephem, an oxacephem, or a prodrug thereof.

In some embodiments, the β-lactam compound is cefazolin, cefalexin, cefadroxil, cefapirin, cefazedone, cefazaflur, cefradine, cefroxadine, ceftezole, cefaloglycin, cefacetrile, cefalonium, cefaloridine, cefalotin, cefatrizine, cefaclor, cefotetan, cephamycin (e.g., cefoxitin, cefprozil, cefuroxime, cefuroxime axetil, cefamandole, cefminox, cefonicid, ceforanide, cefotiam, cefbuperazone, cefuzonam, cefmetazole), carbacephem (e.g., loracarbef), cefixime, ceftriaxone, antipseudomonal (e.g, ceftazidime, cefoperazone), cefdinir, cefcapene, cefdaloxime, ceftizoxime, cefmenoxime, cefotaxime, cefpiramide, cefpodoxime, ceftibuten, cefditoren, cefetamet, cefodizime, cefpimizole, cefsulodin, cefteram, ceftiolene, oxacephem (e.g., flomoxef, latamoxef), cefepime, cefozopran, cefpirome, cefquinome, ceftaroline fosamil, ceftolozane, ceftobiprole, ceftiofur, cefquinome, cefovecin, a pharmaceutically acceptable salt thereof, a prodrug thereof, an analog thereof, or a derivative thereof.

In some embodiments, the β-lactam compound is a thiopenem or a prodrug thereof.

In some embodiments, the β-lactam compound is of Formula (I):

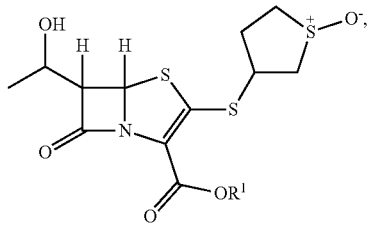

(I)

a pharmaceutically acceptable salt thereof, a prodrug thereof, an analog thereof, or a derivative thereof, wherein $R^1$ is H or optionally substituted alkyl.

In some embodiments, the β-lactam compound is of Formula (Ia):

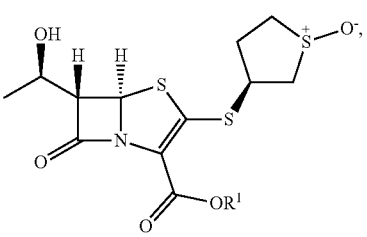

(Ia)

a pharmaceutically acceptable salt thereof, a prodrug thereof, an analog thereof, or a derivative thereof.

In some embodiments, the β-lactam compound is of Formula (Ib):

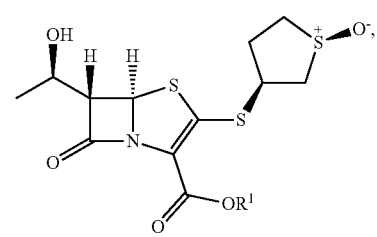

(Ib)

a pharmaceutically acceptable salt thereof, a prodrug thereof, an analog thereof, or a derivative thereof.

In some embodiments, $R^1$ is H.

In some embodiments, the β-lactam compound is of Formula (II):

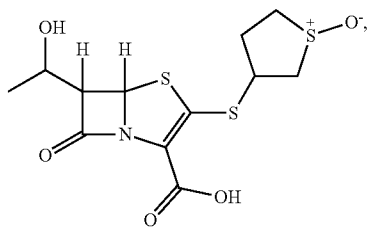

(II)

a pharmaceutically acceptable salt thereof, a prodrug thereof, an analog thereof, or a derivative thereof.

In some embodiments, the β-lactam compound is of Formula (IIa):

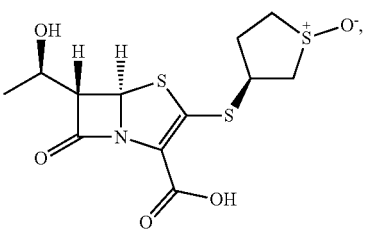

(IIa)

a pharmaceutically acceptable salt thereof, a prodrug thereof, an analog thereof, or a derivative thereof.

In some embodiments, the β-lactam compound is of Formula (IIb):

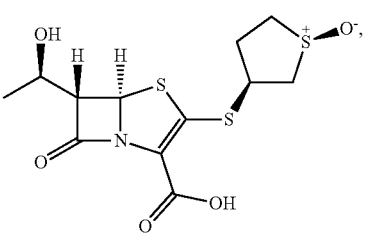

(IIb)

a pharmaceutically acceptable salt thereof, a prodrug thereof, an analog thereof, or a derivative thereof.

In some embodiments, $R^1$ is optionally substituted alkyl.

In some embodiments, the β-lactam compound is of any one of Formulae (III), (IIIa), and (IIIb):

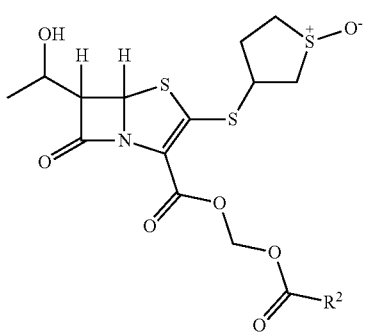

(III)

(IIIa)

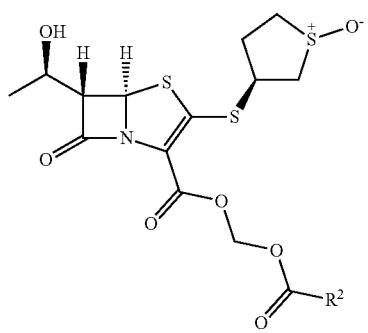

(IIIb)

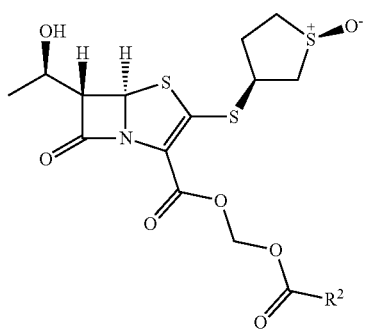

a pharmaceutically acceptable salt thereof, a prodrug thereof, an analog thereof, or a derivative thereof, wherein $R^2$ is H or optionally substituted alkyl.

In some embodiments, the β-lactam compound is selected from the group consisting of:

(Compound III-1)

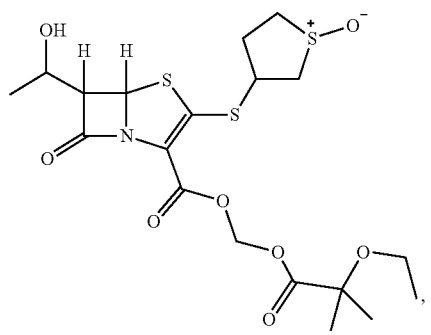

(Compound III-1a)

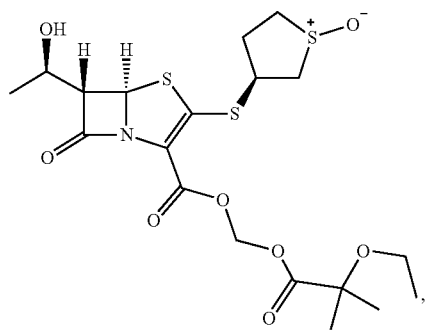

(Compound III-1b)

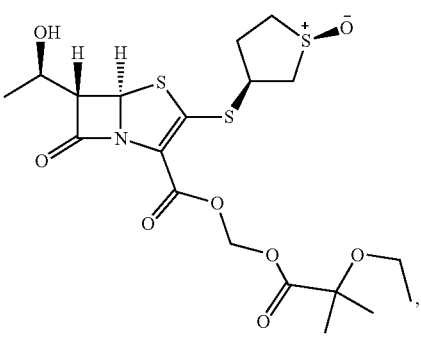

pharmaceutically acceptable salts thereof, prodrugs thereof, analogs thereof, and derivatives thereof.

In some embodiments, the β-lactam compound is selected from the group consisting of:

(Compound III-2)

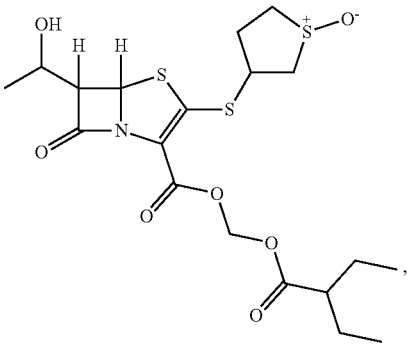

(Compound III-2a)

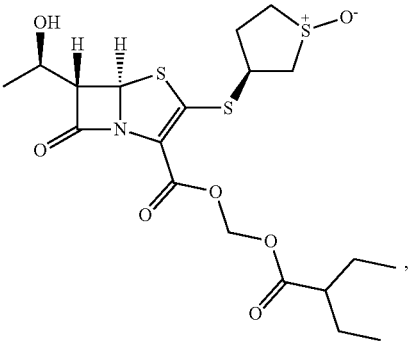

(Compound III-2b)

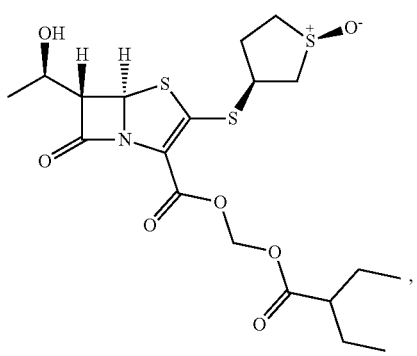

pharmaceutically acceptable salts thereof, prodrugs thereof, analogs thereof, and derivatives thereof.

In some embodiments, the β-lactam compound is selected from:

(Compound III-2b; also known as Sulopenem Etzadroxil)

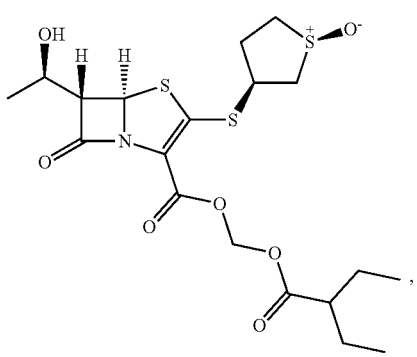

pharmaceutically acceptable salts thereof, prodrugs thereof, analogs thereof, and derivatives thereof.

In some embodiments, the β-lactam compound is (Compound III-2b; also known as Sulopenem Etzadroxil)

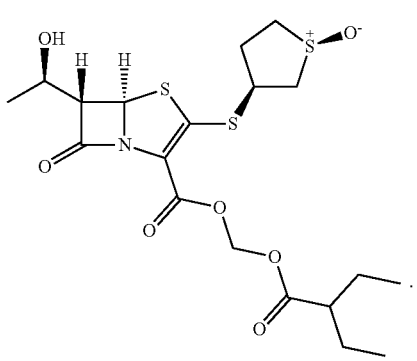

In some embodiments, the β-lactam compound is of any one of Formulae (IV), (IVa), and (IVb):

(IV)

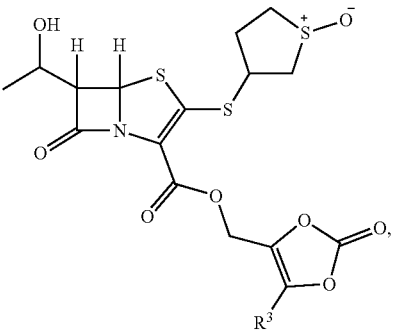

(IVa)

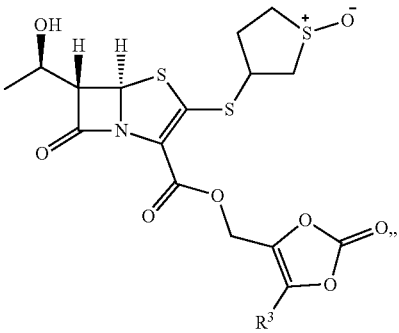

(IVb)

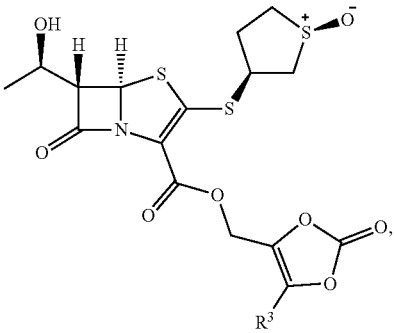

a pharmaceutically acceptable salt thereof, a prodrug thereof, an analog thereof, or a derivative thereof, wherein $R^3$ is H or optionally substituted alkyl.

In some embodiments, $R^3$ is $C_2$-$C_8$ alkyl.

In some embodiments, $R^3$ is $CH_2CH_3$, $CH_2CH_2CH_3$, or $CH_2CH(CH_3)_2$.

In some embodiments, the pharmaceutical salt of the β-lactam compound is a sodium salt, a potassium salt, a lithium salt, an ammonium salt, a calcium salt, a magnesium salt, an iron salt, a zinc salt, a copper salt, a manganese salt, or an aluminum salt.

It is understood that valproic acid is of the following structure:

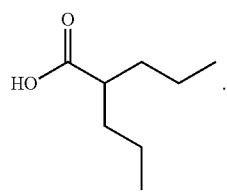

In some embodiments, the pharmaceutical salt of valproic acid is a sodium salt, a potassium salt, a lithium salt, an ammonium salt, a calcium salt, a magnesium salt, an iron salt, a zinc salt, a copper salt, a manganese salt, or an aluminum salt.

It is understood that probenecid (e.g., sold under the brandname Probalan) is of the following structure:

[Chemical structure of probenecid]

In some embodiments, the pharmaceutical salt of probenecid is a sodium salt, a potassium salt, a lithium salt, an ammonium salt, a calcium salt, a magnesium salt, an iron salt, a zinc salt, a copper salt, a manganese salt, or an aluminum salt.

Administrations of Valproic Acid, β-Lactam Compounds, and Probenecid

In some embodiments, valproic acid or the pharmaceutically acceptable salt thereof is administered one or more times daily at a daily dosage of about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 20 mg, about 30 mg, about 40 mg, about 50 mg, about 60 mg, about 70 mg, about 80 mg, about 90 mg, about 100 mg, about 200 mg, about 300 mg, about 400 mg, about 500 mg, about 600 mg, about 700 mg, about 800 mg, about 900 mg, about 1 g, about 2 g, about 3 g, about 4 g, about 5 g, about 6 g, about 7 g, about 8 g, about 9 g, about 10 g, about 20 g, about 30 g, about 40 g, or about 50 g.

In some embodiments, valproic acid or the pharmaceutically acceptable salt thereof is administered once daily, twice daily, or three or more times daily.

In some embodiments, valproic acid or the pharmaceutically acceptable salt thereof is administered continuously.

In some embodiments, valproic acid or the pharmaceutically acceptable salt thereof is administered for more than about 1 day.

In some embodiments, valproic acid or the pharmaceutically acceptable salt thereof is administered for about 2 days, about 3 days, about 4 days, about 5 days, about 6 days, about 7 days, about 14 days, or about 30 days.

In some embodiments, valproic acid or the pharmaceutically acceptable salt thereof is administered with one or more drug holidays.

In some embodiments, valproic acid or the pharmaceutically acceptable salt thereof is administered without any drug holiday.

In some embodiments, valproic acid or the pharmaceutically acceptable salt thereof is administered by an enteral administration.

In some embodiments, valproic acid or the pharmaceutically acceptable salt thereof is administered by an oral administration or a rectum administration.

In some embodiments, valproic acid or the pharmaceutically acceptable salt thereof is administered by an oral administration.

In some embodiments, valproic acid or the pharmaceutically acceptable salt thereof is administered by a parenteral administration.

In some embodiments, valproic acid or the pharmaceutically acceptable salt thereof is administered injection (e.g., intravenous infusion).

In some embodiments, valproic acid or the pharmaceutically acceptable salt thereof is administered by an intravenous administration.

In some embodiments, the β-lactam compound or the pharmaceutically acceptable salt thereof is administered one or more times daily at a daily dosage of about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 20 mg, about 30 mg, about 40 mg, about 50 mg, about 60 mg, about 70 mg, about 80 mg, about 90 mg, about 100 mg, about 200 mg, about 300 mg, about 400 mg, about 500 mg, about 600 mg, about 700 mg, about 800 mg, about 900 mg, about 1 g, about 2 g, about 3 g, about 4 g, about 5 g, about 6 g, about 7 g, about 8 g, about 9 g, about 10 g, about 20 g, about 30 g, about 40 g, or about 50 g.

In some embodiments, the β-lactam compound or the pharmaceutically acceptable salt thereof is administered once daily, twice daily, or three or more times daily.

In some embodiments, the β-lactam compound or the pharmaceutically acceptable salt thereof is administered continuously.

In some embodiments, the β-lactam compound or the pharmaceutically acceptable salt thereof is administered for more than about 1 day.

In some embodiments, the β-lactam compound or the pharmaceutically acceptable salt thereof is administered for about 2 days, about 3 days, about 4 days, about 5 days, about 6 days, about 7 days, about 14 days, or about 30 days.

In some embodiments, the β-lactam compound or the pharmaceutically acceptable salt thereof is administered with one or more drug holidays.

In some embodiments, the β-lactam compound or the pharmaceutically acceptable salt thereof is administered without any drug holiday.

In some embodiments, the β-lactam compound or the pharmaceutically acceptable salt thereof is administered by an enteral administration.

In some embodiments, the β-lactam compound or the pharmaceutically acceptable salt thereof is administered by an oral administration or a rectum administration.

In some embodiments, the β-lactam compound or the pharmaceutically acceptable salt thereof is administered by an oral administration.

In some embodiments, the β-lactam compound or the pharmaceutically acceptable salt thereof is administered by a parenteral administration.

In some embodiments, the β-lactam compound or the pharmaceutically acceptable salt thereof is administered injection (e.g., intravenous infusion).

In some embodiments, the β-lactam compound or the pharmaceutically acceptable salt thereof is administered by an intravenous administration.

In some embodiments, probenecid or the pharmaceutically acceptable salt thereof is administered one or more times daily at a daily dosage of about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 20 mg, about 30 mg, about 40 mg, about 50 mg, about 60 mg, about 70 mg, about 80 mg, about 90 mg, about 100 mg, about 200 mg, about 300 mg, about 400 mg, about 500 mg, about 600 mg, about 700 mg, about 800 mg, about 900 mg, about 1 g, about 2 g, about 3 g, about 4 g, about 5 g, about 6 g, about 7 g, about 8 g, about 9 g, about 10 g, about 20 g, about 30 g, about 40 g, or about 50 g.

In some embodiments, probenecid or the pharmaceutically acceptable salt thereof is administered once daily, twice daily, or three or more times daily.

In some embodiments, probenecid or the pharmaceutically acceptable salt thereof is administered continuously.

In some embodiments, probenecid or the pharmaceutically acceptable salt thereof is administered for more than about 1 day.

In some embodiments, probenecid or the pharmaceutically acceptable salt thereof is administered for about 2 days, about 3 days, about 4 days, about 5 days, about 6 days, about 7 days, about 14 days, or about 30 days.

In some embodiments, probenecid or the pharmaceutically acceptable salt thereof is administered with one or more drug holidays.

In some embodiments, probenecid or the pharmaceutically acceptable salt thereof is administered without any drug holiday.

In some embodiments, probenecid or the pharmaceutically acceptable salt thereof is administered by an enteral administration.

In some embodiments, probenecid or the pharmaceutically acceptable salt thereof is administered by an oral administration or a rectum administration.

In some embodiments, probenecid or the pharmaceutically acceptable salt thereof is administered by an oral administration.

In some embodiments, probenecid or the pharmaceutically acceptable salt thereof is administered by a parenteral administration.

In some embodiments, probenecid or the pharmaceutically acceptable salt thereof is administered injection (e.g., intravenous infusion).

In some embodiments, probenecid or the pharmaceutically acceptable salt thereof is administered by an intravenous administration.

In some embodiments, valproic acid or the pharmaceutically acceptable salt thereof, the β-lactam compound or the pharmaceutically acceptable salt thereof, and probenecid or the pharmaceutically acceptable salt thereof are administered simultaneously or sequentially.

In some embodiments, valproic acid or the pharmaceutically acceptable salt thereof and probenecid or the pharmaceutically acceptable salt thereof are administered simultaneously, sequentially, or in alternation.

In some embodiments, valproic acid or the pharmaceutically acceptable salt thereof and the β-lactam compound or the pharmaceutically acceptable salt thereof are administered simultaneously, sequentially, or in alternation.

In some embodiments, the β-lactam compound or the pharmaceutically acceptable salt thereof and probenecid or the pharmaceutically acceptable salt thereof are administered simultaneously, sequentially, or in alternation.

In some embodiments, the β-lactam compound or the pharmaceutically acceptable salt thereof and probenecid or the pharmaceutically acceptable salt thereof are administered simultaneously.

In some embodiments, the β-lactam compound or the pharmaceutically acceptable salt thereof and probenecid or the pharmaceutically acceptable salt thereof are administered sequentially.

In some embodiments, the valproic acid or the pharmaceutically acceptable salt thereof, the β-lactam compound or the pharmaceutically acceptable salt thereof, and probenecid or the pharmaceutically acceptable salt thereof are administered simultaneously.

In some embodiments, the valproic acid or the pharmaceutically acceptable salt thereof and the β-lactam compound or the pharmaceutically acceptable salt thereof are administered simultaneously.

In some embodiments, the valproic acid or the pharmaceutically acceptable salt thereof and probenecid or the pharmaceutically acceptable salt thereof are administered simultaneously.

In some embodiments, the β-lactam compound or the pharmaceutically acceptable salt thereof and probenecid or the pharmaceutically acceptable salt thereof are administered simultaneously.

In some embodiments, the valproic acid or the pharmaceutically acceptable salt thereof and the β-lactam compound or the pharmaceutically acceptable salt thereof are administered simultaneously, followed by administration of probenecid or a pharmaceutically acceptable salt thereof.

In some embodiments, the valproic acid or the pharmaceutically acceptable salt thereof and the β-lactam compound or the pharmaceutically acceptable salt thereof are administered simultaneously, after administration of probenecid or a pharmaceutically acceptable salt thereof.

In some embodiments, the valproic acid or the pharmaceutically acceptable salt thereof and probenecid or the pharmaceutically acceptable salt thereof are administered simultaneously, followed by administration of the β-lactam compound or a pharmaceutically acceptable salt thereof.

In some embodiments, the valproic acid or the pharmaceutically acceptable salt thereof and probenecid or the pharmaceutically acceptable salt thereof are administered simultaneously, after administration of the β-lactam compound or a pharmaceutically acceptable salt thereof.

In some embodiments, the β-lactam compound or the pharmaceutically acceptable salt thereof and probenecid or the pharmaceutically acceptable salt thereof are administered simultaneously, followed by administration of valproic acid or a pharmaceutically acceptable salt thereof.

In some embodiments, the β-lactam compound or the pharmaceutically acceptable salt thereof and probenecid or the pharmaceutically acceptable salt thereof are administered simultaneously, after administration of valproic acid or a pharmaceutically acceptable salt thereof.

In some embodiments, valproic acid or a pharmaceutically acceptable salt thereof, the β-lactam compound or the pharmaceutically acceptable salt thereof, and probenecid or the pharmaceutically acceptable salt thereof are administered sequentially.

In some embodiments, valproic acid or a pharmaceutically acceptable salt thereof, probenecid compound or the pharmaceutically acceptable salt thereof, and the β-lactam or the pharmaceutically acceptable salt thereof are administered sequentially.

In some embodiments, the β-lactam compound or the pharmaceutically acceptable salt thereof, valproic acid or a pharmaceutically acceptable salt thereof, and probenecid or the pharmaceutically acceptable salt thereof are administered sequentially.

In some embodiments, the β-lactam compound or the pharmaceutically acceptable salt thereof, probenecid or the pharmaceutically acceptable salt thereof, and valproic acid or a pharmaceutically acceptable salt thereof are administered sequentially.

In some embodiments, probenecid or the pharmaceutically acceptable salt thereof, the β-lactam or the pharmaceutically acceptable salt thereof, and valproic acid or a pharmaceutically acceptable salt thereof are administered sequentially.

In some embodiments, probenecid or the pharmaceutically acceptable salt thereof, valproic acid or the pharmaceutically acceptable salt thereof, and the β-lactam or a pharmaceutically acceptable salt thereof are administered sequentially.

In some embodiments, valproic acid or the pharmaceutically acceptable salt thereof, the β-lactam compound or the pharmaceutically acceptable salt thereof, and probenecid or the pharmaceutically acceptable salt thereof are administered in temporal proximity.

In some embodiments, valproic acid or the pharmaceutically acceptable salt thereof and the β-lactam compound or the pharmaceutically acceptable salt thereof are administered in temporal proximity.

In some embodiments, valproic acid or the pharmaceutically acceptable salt thereof and probenecid or the pharmaceutically acceptable salt thereof are administered in temporal proximity.

In some embodiments, β-lactam compound or the pharmaceutically acceptable salt thereof, and probenecid or the pharmaceutically acceptable salt thereof are administered in temporal proximity.

In some embodiments, the β-lactam compound or the pharmaceutically acceptable salt thereof is administered prior to the administration of probenecid or the pharmaceutically acceptable salt thereof.

In some embodiments, probenecid or the pharmaceutically acceptable salt thereof is administered prior to the administration of the β-lactam compound or the pharmaceutically acceptable salt thereof.

In some embodiments, the valproic acid or the pharmaceutically acceptable salt thereof, the β-lactam compound or the pharmaceutically acceptable salt thereof, and probenecid or the pharmaceutically acceptable salt thereof are administered by the same route.

In some embodiments, the valproic acid or the pharmaceutically acceptable salt thereof and the β-lactam compound or the pharmaceutically acceptable salt thereof are administered by the same route.

In some embodiments, the valproic acid or the pharmaceutically acceptable salt thereof and probenecid or the pharmaceutically acceptable salt thereof are administered by the same route.

In some embodiments, the β-lactam compound or the pharmaceutically acceptable salt thereof and probenecid or the pharmaceutically acceptable salt thereof are administered by the same route.

In some embodiments, the valproic acid or the pharmaceutically acceptable salt thereof, the β-lactam compound or the pharmaceutically acceptable salt thereof, and probenecid or the pharmaceutically acceptable salt thereof are administered by different routes.

In some embodiments, the valproic acid or the pharmaceutically acceptable salt thereof and the β-lactam compound or the pharmaceutically acceptable salt thereof are administered by different routes.

In some embodiments, the valproic acid or the pharmaceutically acceptable salt thereof and probenecid or the pharmaceutically acceptable salt thereof are administered by different routes.

In some embodiments, the β-lactam compound or the pharmaceutically acceptable salt thereof and probenecid or the pharmaceutically acceptable salt thereof are administered by different routes.

In some embodiments, valproic acid or the pharmaceutically acceptable salt thereof, the β-lactam compound or the pharmaceutically acceptable salt thereof, and probenecid or the pharmaceutically acceptable salt thereof are administered by enteral administration.

In some embodiments, valproic acid or the pharmaceutically acceptable salt thereof and the β-lactam compound or the pharmaceutically acceptable salt thereof are administered by enteral administration.

In some embodiments, valproic acid or the pharmaceutically acceptable salt thereof and probenecid or the pharmaceutically acceptable salt thereof are administered by enteral administration.

In some embodiments, probenecid or the pharmaceutically acceptable salt thereof and the β-lactam compound or the pharmaceutically acceptable salt thereof are administered by enteral administration.

In some embodiments, valproic acid or the pharmaceutically acceptable salt thereof is administered enterally.

In some embodiments, probenecid or the pharmaceutically acceptable salt thereof is administered enterally.

In some embodiments, the β-lactam compound or the pharmaceutically acceptable salt thereof is administered enterally.

In some embodiments, the enteral administration is oral administration.

In some embodiments, valproic acid or the pharmaceutically acceptable salt thereof, the β-lactam compound or the pharmaceutically acceptable salt thereof, and probenecid or the pharmaceutically acceptable salt thereof are administered orally.

In some embodiments, valproic acid or the pharmaceutically acceptable salt thereof and the β-lactam compound or the pharmaceutically acceptable salt thereof are administered orally.

In some embodiments, valproic acid or the pharmaceutically acceptable salt thereof and probenecid or the pharmaceutically acceptable salt thereof are administered orally.

In some embodiments, probenecid or the pharmaceutically acceptable salt thereof and the β-lactam compound or the pharmaceutically acceptable salt thereof are administered orally.

In some embodiments, valproic acid or the pharmaceutically acceptable salt thereof is administered orally.

In some embodiments, probenecid or the pharmaceutically acceptable salt thereof is administered orally.

In some embodiments, the β-lactam compound or the pharmaceutically acceptable salt thereof is administered orally.

In some embodiments, an oral co-formulation comprising valproic acid or a pharmaceutically acceptable salt thereof, the β-lactam compound or the pharmaceutically acceptable salt thereof, and probenecid or the pharmaceutically acceptable salt thereof is administered.

In some embodiments, an oral co-formulation comprising valproic acid or a pharmaceutically acceptable salt thereof and the β-lactam compound or the pharmaceutically acceptable salt thereof is administered.

In some embodiments, an oral co-formulation comprising valproic acid or a pharmaceutically acceptable salt thereof and probenecid or the pharmaceutically acceptable salt thereof is administered.

In some embodiments, an oral co-formulation comprising the β-lactam compound or the pharmaceutically acceptable salt thereof and probenecid or the pharmaceutically acceptable salt thereof is administered.

In some embodiments, the oral co-formulation is administered to the subject one or more times daily.

In some embodiments, the oral co-formulation is administered to the subject once daily.

In some embodiments, a tablet comprising valproic acid or a pharmaceutically acceptable salt thereof, the β-lactam compound or the pharmaceutically acceptable salt thereof, and probenecid or the pharmaceutically acceptable salt thereof is administered.

In some embodiments, a tablet comprising valproic acid or a pharmaceutically acceptable salt thereof and the β-lactam compound or the pharmaceutically acceptable salt thereof is administered.

In some embodiments, a tablet comprising valproic acid or a pharmaceutically acceptable salt thereof and probenecid or the pharmaceutically acceptable salt thereof is administered.

In some embodiments, a tablet comprising the β-lactam compound or the pharmaceutically acceptable salt thereof and probenecid or the pharmaceutically acceptable salt thereof is administered.

In some embodiments, the tablet is a bilayer tablet comprising:
    a second layer comprising the β-lactam compound or the pharmaceutically acceptable salt thereof; and
    a first layer comprising probenecid or the pharmaceutically acceptable salt thereof.

In some embodiments, the first layer comprises from 20 mg to about 5 g, from about 50 mg to about 2 g, from about 80 mg to about 1 g, from about 100 mg to about 900 mg, from about 200 mg to about 800 mg, from about 300 mg to about 700 mg, from about 400 mg to about 600 mg, from about 450 mg to about 550 mg, or from about 480 mg to about 520 mg of probenecid or the pharmaceutically acceptable salt thereof.

In some embodiments, the second layer comprises from 20 mg to about 5 g, from about 50 mg to about 2 g, from about 80 mg to about 1 g, from about 100 mg to about 900 mg, from about 200 mg to about 800 mg, from about 300 mg to about 700 mg, from about 400 mg to about 600 mg, from about 450 mg to about 550 mg, or from about 480 mg to about 520 mg of the β-lactam compound (e.g., Compound III-2, Compound III-2a, or Compound III-2b) or the pharmaceutically acceptable salt thereof.

In some embodiments, the first layer comprises about 500±450 mg, about 500±400 mg, about 500±350 mg, about 500±300 mg, about 500±250 mg, about 500±200 mg, about 500±150 mg, about 500±100 mg, about 500±90 mg, about 500±80 mg, about 500±70 mg, about 500±60 mg, about 500±50 mg, about 500±45 mg, about 500±40 mg, about 500±35 mg, about 500±30 mg, about 500±25 mg, about 500±20 mg, about 500±15 mg, about 500±10 mg, or about 500±5 mg of probenecid or the pharmaceutically acceptable salt thereof.

In some embodiments, the second layer comprises about 500±400 mg, about 500±350 mg, about 500±300 mg, about 500±250 mg, about 500±200 mg, about 500±150 mg, about 500±100 mg, about 500±90 mg, about 500±80 mg, about 500±70 mg, about 500±60 mg, about 500±50 mg, about 500±45 mg, about 500±40 mg, about 500±35 mg, about 500±30 mg, about 500±25 mg, about 500±20 mg, about 500±15 mg, about 500±10 mg, or about 500±5 mg of the β-lactam compound (e.g., Compound III-2, Compound III-2a, or Compound III-2b) or the pharmaceutically acceptable salt thereof.

In some embodiments, the first layer comprises about 500 mg of probenecid or the pharmaceutically acceptable salt thereof.

In some embodiments, the second layer comprises about 500 mg of the β-lactam compound (e.g., Compound III-2, Compound III-2a, or Compound III-2b) or the pharmaceutically acceptable salt thereof.

In some embodiments, bilayer tablet further comprises one or more of pharmaceutical excipients.

In some embodiments, the one or more of pharmaceutical excipients are selected from cellulose, sodium croscamellose, magnesium stearate, lactose monohydrate, and hydroxypropylcellulose.

In some embodiments, the bilayer tablet is administered to the subject one or more times daily.

In some embodiments, the bilayer tablet is administered to the subject once daily.

In some embodiments, a tablet comprising valproic acid or the pharmaceutically acceptable salt thereof is administered.

In some embodiments, a tablet comprising the β-lactam compound or the pharmaceutically acceptable salt thereof is administered.

In some embodiments, a tablet comprising probenecid or the pharmaceutically acceptable salt thereof is administered.

In some embodiments, the tablets are administered to the subject one or more times daily.

In some embodiments, the tablets are administered to the subject once daily.

In some embodiments, valproic acid or the pharmaceutically acceptable salt thereof, the β-lactam compound or the pharmaceutically acceptable salt thereof, and probenecid or the pharmaceutically acceptable salt thereof are administered in separate oral formulations.

In some embodiments, a tablet comprising valproic acid or a pharmaceutically acceptable salt thereof and the β-lactam compound or the pharmaceutically acceptable salt thereof are both administered in separate oral formulations.

In some embodiments, a tablet comprising valproic acid or a pharmaceutically acceptable salt thereof and probenecid or the pharmaceutically acceptable salt thereof are both administered in separate oral formulations.

In some embodiments, a tablet comprising the β-lactam compound or the pharmaceutically acceptable salt thereof and probenecid or the pharmaceutically acceptable salt thereof are both administered in separate oral formulations.

In some embodiments, the separate oral formulations are administered to the subject one or more times daily.

In some embodiments, the separate oral formulations are administered to the subject once daily.

In some embodiments, valproic acid or the pharmaceutically acceptable salt thereof, the β-lactam compound or the pharmaceutically acceptable salt thereof, and probenecid or the pharmaceutically acceptable salt thereof are administered in separate tablets.

In some embodiments, a tablet comprising valproic acid or a pharmaceutically acceptable salt thereof and the β-lactam compound or the pharmaceutically acceptable salt thereof are both administered in separate tablets.

In some embodiments, a tablet comprising valproic acid or a pharmaceutically acceptable salt thereof and probenecid or the pharmaceutically acceptable salt thereof are both administered in separate tablets.

In some embodiments, the β-lactam compound or the pharmaceutically acceptable salt thereof and probenecid or the pharmaceutically acceptable salt thereof are both administered in separate tablets.

In some embodiments, the tablets are administered to the subject one or more times daily.

In some embodiments, the tablets are administered to the subject once daily.

In some embodiments, valproic acid or the pharmaceutically acceptable salt thereof, the β-lactam compound or the pharmaceutically acceptable salt thereof, and probenecid or the pharmaceutically acceptable salt thereof are administered by parenteral administration.

In some embodiments, valproic acid or the pharmaceutically acceptable salt thereof and the β-lactam compound or the pharmaceutically acceptable salt thereof are administered by parenteral administration.

In some embodiments, valproic acid or the pharmaceutically acceptable salt thereof and probenecid or the pharmaceutically acceptable salt thereof are administered by parenteral administration.

In some embodiments, the β-lactam compound or the pharmaceutically acceptable salt thereof, and probenecid or the pharmaceutically acceptable salt thereof are administered by parenteral administration.

In some embodiments, valproic acid or the pharmaceutically acceptable salt thereof is administered by parenteral administration.

In some embodiments, β-lactam compound or the pharmaceutically acceptable salt thereof is administered by parenteral administration.

In some embodiments, probenecid or the pharmaceutically acceptable salt thereof is administered by parenteral administration.

In some embodiments, the parenteral administration is intravenous administration.

In some embodiments, valproic acid or the pharmaceutically acceptable salt thereof, the β-lactam compound or the pharmaceutically acceptable salt thereof, and probenecid or the pharmaceutically acceptable salt thereof are administered intravenously.

In some embodiments, valproic acid or the pharmaceutically acceptable salt thereof and the β-lactam compound or the pharmaceutically acceptable salt thereof are administered intravenously.

In some embodiments, valproic acid or the pharmaceutically acceptable salt thereof and probenecid or the pharmaceutically acceptable salt thereof are administered intravenously.

In some embodiments, the β-lactam compound or the pharmaceutically acceptable salt thereof, and probenecid or the pharmaceutically acceptable salt thereof are administered intravenously.

In some embodiments, valproic acid or the pharmaceutically acceptable salt thereof is administered intravenously.

In some embodiments, β-lactam compound or the pharmaceutically acceptable salt thereof is administered intravenously.

In some embodiments, probenecid or the pharmaceutically acceptable salt thereof is administered intravenously.
In some embodiments, valproic acid or the pharmaceutically acceptable salt thereof, the β-lactam compound or the pharmaceutically acceptable salt thereof, and probenecid or the pharmaceutically acceptable salt thereof are administered in a co-formulation.

In some embodiments, valproic acid or the pharmaceutically acceptable salt thereof and the β-lactam compound or the pharmaceutically acceptable salt thereof are administered in a co-formulation.

In some embodiments, valproic acid or the pharmaceutically acceptable salt thereof and probenecid or the pharmaceutically acceptable salt thereof are administered in a co-formulation.

In some embodiments, the β-lactam compound or the pharmaceutically acceptable salt thereof and probenecid or the pharmaceutically acceptable salt thereof are administered in a co-formulation.

In some embodiments, the co-formulation is administered to the subject one or more times daily.

In some embodiments, the co-formulation is administered to the subject once daily.

In some embodiments, the co-formulation is an oral co-formulation (e.g., a tablet).

In some embodiments, valproic acid or a pharmaceutically acceptable salt thereof, the β-lactam compound or the pharmaceutically acceptable salt thereof, and probenecid or the pharmaceutically acceptable salt thereof are administered in separate formulations.

Exemplary Embodiments of Methods

In some embodiments, the valproic acid or the pharmaceutically acceptable salt thereof is administered at a dosage of about 50 mg per day, about 100 mg per day, about 150 mg per day, about 200 mg per day, about 250 mg per day, about 300 mg per day, about 350 mg per day, about 400 mg per day, about 500 mg per day, about 1 g per day, about 2 g per day, about 3 g per day, about 4 g per day, or about 5 g per day.

In some embodiments, the valproic acid or the pharmaceutically acceptable salt thereof is administered at a dosage of 500±300 mg per day, 500±250 mg per day, 500±200 mg per day, 500±150 mg per day, 500±100 mg per day, 500±90 mg per day, 500±80 mg per day, 500±70 mg per day, 500±60 mg per day, 500±50 mg per day, 500±40 mg per day, 500±30 mg per day, 500±20 mg per day, 500±10 mg per day, 500±5 mg per day, 500±4 mg per day, 500±3 mg per day, 500±2 mg per day, 500±1 mg per day (e.g., about 500 mg per day).

In some embodiments, the β-lactam compound or the pharmaceutically acceptable salt thereof is administered at a dosage of about 50 mg per day, about 100 mg per day, about 150 mg per day, about 200 mg per day, about 250 mg per day, about 300 mg per day, about 350 mg per day, about 400 mg per day, about 500 mg per day, about 1 g per day, about 2 g per day, about 3 g per day, about 4 g per day, or about 5 g per day.

In some embodiments, the β-lactam compound or the pharmaceutically acceptable salt thereof is administered at a dosage of 500±300 mg per day, 500±250 mg per day, 500±200 mg per day, 500±150 mg per day, 500±100 mg per day, 500±90 mg per day, 500±80 mg per day, 500±70 mg per day, 500±60 mg per day, 500±50 mg per day, 500±40 mg per day, 500±30 mg per day, 500±20 mg per day, 500±10 mg per day, 500±5 mg per day, 500±4 mg per day, 500±3 mg per day, 500±2 mg per day, 500±1 mg per day (e.g., about 500 mg per day).

In some embodiments, the probenecid or the pharmaceutically acceptable salt thereof is administered at a dosage of about 50 mg per day, about 100 mg per day, about 150 mg per day, about 200 mg per day, about 250 mg per day, about 300 mg per day, about 350 mg per day, about 400 mg per day, about 500 mg per day, about 1 g per day, about 2 g per day, about 3 g per day, about 4 g per day, or about 5 g per day.

In some embodiments, the probenecid or the pharmaceutically acceptable salt thereof is administered at a dosage of 500±300 mg per day, 500±250 mg per day, 500±200 mg per day, 500±150 mg per day, 500±100 mg per day, 500±90 mg per day, 500±80 mg per day, 500±70 mg per day, 500±60 mg per day, 500±50 mg per day, 500±40 mg per day, 500±30 mg per day, 500±20 mg per day, 500±10 mg per day, 500±5 mg per day, 500±4 mg per day, 500±3 mg per day, 500±2 mg per day, 500±1 mg per day (e.g., about 500 mg per day).

In some embodiments, the valproic acid or the pharmaceutically acceptable salt thereof is administered at a dosage of 500±300 mg per day, 500±250 mg per day, 500±200 mg per day, 500±150 mg per day, 500±100 mg per day, 500±90 mg per day, 500±80 mg per day, 500±70 mg per day, 500±60 mg per day, 500±50 mg per day, 500±40 mg per day, 500±30 mg per day, 500±20 mg per day, 500±10 mg per day, 500±5 mg per day, 500±4 mg per day, 500±3 mg per day, 500±2 mg per day, 500±1 mg per day (e.g., about 500 mg per day);

the β-lactam compound or the pharmaceutically acceptable salt thereof is administered at a dosage of 500±300 mg per day, 500±250 mg per day, 500±200 mg per day, 500±150 mg per day, 500±100 mg per day, 500±90 mg per day, 500±80 mg per day, 500±70 mg per day, 500±60 mg per day, 500±50 mg per day, 500±40 mg per day, 500±30 mg per day, 500±20 mg per day, 500±10 mg per day, 500±5 mg per day, 500±4 mg per day, 500±3 mg per day, 500±2 mg per day, 500±1 mg per day (e.g., about 500 mg per day); and the probenecid or the pharmaceutically acceptable salt thereof is administered at a dosage of 500±300 mg per day, 500±250 mg per day, 500±200 mg per day, 500±150 mg per day, 500±100 mg per day, 500±90 mg per day, 500±80 mg per day, 500±70 mg per day, 500±60 mg per day, 500±50 mg per day, 500±40 mg per day, 500±30 mg per day, 500±20 mg per day, 500±10 mg per day, 500±5 mg per day, 500±4 mg per day, 500±3 mg per day, 500±2 mg per day, 500±1 mg per day (e.g., about 500 mg per day).

Combinations, Pharmaceutical Compositions, and Pharmaceutical Kits

In some aspects, the present disclosure provides a combination comprising:

a pharmaceutically effective amount of valproic acid or a pharmaceutically acceptable salt thereof;

a pharmaceutically effective amount of a β-lactam compound or a pharmaceutically acceptable salt thereof, and a pharmaceutically effective amount of probenecid or a pharmaceutically acceptable salt thereof.

In some aspects, the present disclosure provides a pharmaceutical composition comprising:

a pharmaceutically effective amount of valproic acid or a pharmaceutically acceptable salt thereof;

a pharmaceutically effective amount of a β-lactam compound or a pharmaceutically acceptable salt thereof, and a pharmaceutically effective amount of probenecid or a pharmaceutically acceptable salt thereof.

In some aspects, the present disclosure provides a pharmaceutical kit comprising:

a pharmaceutically effective amount of valproic acid or a pharmaceutically acceptable salt thereof;

a pharmaceutically effective amount of a β-lactam compound or a pharmaceutically acceptable salt thereof, and a pharmaceutically effective amount of probenecid or a pharmaceutically acceptable salt thereof.

Definitions

As used herein, the term "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl. In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl.

As used herein, the term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, and the like. In the case of multicyclic non-aromatic rings, only one of the rings needs to be non-aromatic (e.g., 1,2,3,4-tetrahydronaphthalenyl or 2,3-dihydroindole).

As used herein, the term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

As used herein, the term "aryl" includes groups with aromaticity, including "conjugated," or multicyclic systems with one or more aromatic rings and do not contain any heteroatom in the ring structure. Examples include phenyl, naphthalenyl, etc.

As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1. Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthrydine, indole, benzofuran, purine, benzofuran, deazapurine, indolizine.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the term "heterocycle" or "heterocyclic group" includes any ring structure (saturated, unsaturated, or aromatic) which contains at least one ring heteroatom (e.g., 1-4 heteroatoms selected from N, O and S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl (e.g., benzo[d][1,3]dioxole-5-yl), morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

As used herein, the term "hydroxy" or "hydroxyl" includes groups with an —OH or —O.

As used herein, the term "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

As used herein, the term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

As used herein, the term "carboxyl" refers to —COOH or its $C_1$-$C_6$ alkyl ester.

As used herein, the term "acyl" includes moieties that contain the acyl radical (R—C(O)—) or a carbonyl group. As used herein, the term "substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

As used herein, the term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

As used herein, the term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

As used herein, the term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

As used herein, the term "thiocarbonyl" or "thiocarboxy" includes compounds and moieties which contain a carbon connected with a double bond to a sulfur atom.

As used herein, the term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, the term "amine" or "amino" refers to —$NH_2$. "Alkylamino" includes groups of compounds wherein the nitrogen of —$NH_2$ is bound to at least one alkyl group.

Examples of alkylamino groups include benzylamino, methylamino, ethylamino, phenethylamino, etc.

As used herein, the term "dialkylamino" includes groups wherein the nitrogen of —$NH_2$ is bound to two alkyl groups. Examples of dialkylamino groups include, but are not limited to, dimethylamino and diethylamino.

As used herein, the terms "arylamino" and "diarylamino" include groups wherein the nitrogen is bound to at least one or two aryl groups, respectively.

As used herein, the terms "aminoaryl" and "aminoaryloxy" refer to aryl and aryloxy substituted with amino.

As used herein, the terms "alkylarylamino," "alkylaminoaryl" or "arylaminoalkyl" refers to an amino group which is bound to at least one alkyl group and at least one aryl group.

As used herein, the terms "alkaminoalkyl" refers to an alkyl, alkenyl, or alkynyl group bound to a nitrogen atom which is also bound to an alkyl group.

As used herein, the terms "acylamino" includes groups wherein nitrogen is bound to an acyl group. Examples of acylamino include, but are not limited to, alkylcarbonylamino, arylcarbonylamino, carbamoyl and ureido groups.

As used herein, the term "amide" or "aminocarboxy" includes compounds or moieties that contain a nitrogen atom that is bound to the carbon of a carbonyl or a thiocarbonyl group.

As used herein, the term "alkaminocarboxy" includes alkyl, alkenyl or alkynyl groups bound to an amino group which is bound to the carbon of a carbonyl or thiocarbonyl group.

As used herein, the term "arylaminocarboxy" includes aryl or heteroaryl moieties bound to an amino group that is bound to the carbon of a carbonyl or thiocarbonyl group.

As used herein, the terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group.

Amides can be substituted with substituents such as straight chain alkyl, branched alkyl, cycloalkyl, aryl, heteroaryl or heterocycle. Substituents on amide groups may be further substituted.

Compounds of the present disclosure that contain nitrogens can be converted to N-oxides by treatment with an oxidizing agent (e.g., 3-chloroperoxybenzoic acid (mCPBA) and/or hydrogen peroxides) to afford other compounds of the present disclosure. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present disclosure can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy derivatives.

In the present specification, the structural formula of the compound represents a certain isomer for convenience in some cases, but the present disclosure includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present disclosure.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral center" refers to a carbon atom bonded to four nonidentical substituents.

As used herein, the term "chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

As used herein, the term "geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

It is to be understood that the structures and other compounds discussed in this disclosure include all atropic isomers thereof. It is also to be understood that not all atropic isomers may have the same level of activity.

As used herein, the term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertible by tautomerizations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

As used herein, the term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

It is to be understood that the compounds of any Formula described herein include the compounds themselves, as well as their salts, and their solvates, if applicable. A salt, for example, can be formed between an anion and a positively charged group (e.g., amino) on a substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

As used herein, the term "pharmaceutically acceptable anion" refers to an anion suitable for forming a pharmaceutically acceptable salt. Likewise, a salt can also be formed between a cation and a negatively charged group (e.g., carboxylate) on a substituted benzene compound. Suitable cations include sodium ion, potassium ion, magnesium ion, calcium ion, and an ammonium cation such as tetramethyl-ammonium ion. The substituted benzene compounds also include those salts containing quaternary nitrogen atoms.

It is to be understood that the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As used herein, the term "derivative" refers to compounds that have a common core structure, and are substituted with various groups as described herein.

As used herein, the term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

It is to be understood that the present disclosure is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

As used herein, the term "substantially the same" refers to a value falling within any normal range over the referenced value (e.g., a value in a comparable subject) as being appreciated by one of ordinary skill in the relevant art. In some embodiments, the term "substantially the same" refers to a value falling within a range from about 40% to about 160%, from about 50% to about 150%, from about 60% to about 140%, from about 70% to about 130%, from about 80% to about 120%, from about 90% to about 110%, or from about 95% to about 105% of the referenced value (e.g., a value in a comparable subject). In some embodiments, the term "substantially the same" refers to a value being about 50%, about 60%, about 70%, about 80%, about 90%, about 95%, about 98%, about 102%, about 105%, about 110%, about 115%, about 120%, about 125%, about 130%, about 140%, or about 150% of the referenced value (e.g., a value in a comparable subject).

It is to be understood that the present disclosure provides methods for the synthesis of the compounds of any of the Formulae described herein. The present disclosure also provides detailed methods for the synthesis of various disclosed compounds of the present disclosure according to the following schemes as well as those shown in the Examples.

It is to be understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

It is to be understood that the synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* 5$^{th}$ edition, John Wiley & Sons: New York, 2001; Greene, T. W., Wuts, P. G. M., *Protective Groups in Organic Synthesis,* 3$^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art One of ordinary skill in the art will note that, during the reaction sequences and synthetic schemes described herein, the order of certain steps may be changed, such as the introduction and removal of protecting groups. One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis,* 3$^{rd}$ edition, John Wiley & Sons: New York, 1999.

It is to be understood that, unless otherwise stated, any description of a method of treatment includes use of the compounds to provide such treatment or prophylaxis as is described herein, as well as use of the compounds to prepare a medicament to treat or prevent such condition. The treatment includes treatment of human or non-human animals including rodents and other disease models.

As used herein, the term "subject" is interchangeable with the term "subject in need thereof", both of which refer to a subject having a disease or having an increased risk of developing the disease. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human.

As used herein, the term "comparable subject" refers to a subject with comparable parameters, or in comparable conditions, as of the subject being compared (e.g., the subject being treated). For example, the "comparable subject" may have a disease as of the subject being compared, or have an increased risk of developing the disease as of the subject being compared. For another example, the "comparable subject" may exhibit one or more plasma pharmakinetic parameters (e.g., $C_{max}$ or AUC) to one or more pharmaceutical agents (e.g., a β-lactam compound, probenecid, or a combination thereof) as of the subject being compared. In some embodiments, the "comparable subject" may be the subject being compared at a different time, e.g., the subject being treated (e.g., by administrating a combination of β-lactam compound, probenecid, and/or valproic acid) may be subjected to conditions (e.g., administration of a β-lactam compound and probenecid without valproic acid) as a "comparable subject" prior to the treatment. In some embodiments, the "comparable subject" may be the subject being compared at a different time, e.g., the subject being treated (e.g., by administrating a combination of β-lactam compound, probenecid, and/or valproic acid) may be subjected to conditions (e.g., administration of a β-lactam compound and valproic acid without probenecid) as a "comparable subject" prior to the treatment. In some embodiments, the "comparable subject" may be the subject being compared at a different time, e.g., the subject being treated (e.g., by administrating a combination of β-lactam compound, probenecid, and/or valproic acid) may be subjected to conditions (e.g., administration of valproic acid and probenecid without a β-lactam compound) as a "comparable subject" prior to the treatment. In some embodiments, the "comparable subject" may be the subject being compared at a different time, e.g., the subject being treated (e.g., by administrating a combination of β-lactam compound and/or valproic acid) may be subjected to conditions (e.g., administration of a β-lactam compound without valproic acid) as a "comparable subject" prior to the treatment. In some embodiments, the "comparable subject" may be the subject being compared at a different time, e.g., the subject being treated (e.g., by administrating a combination of β-lactam compound and/or probenecid) may be subjected to conditions (e.g., administration of a β-lactam compound without probenecid) as a "comparable subject" prior to the treatment. In some embodiments, the "comparable subject" may be the subject being compared at a different time, e.g., the subject being treated (e.g., by administrating a combination of probenecid and/or a β-lactam compound) may be subjected to conditions (e.g., administration of probenecid without a β-lactam compound) as a "comparable subject" prior to the treatment. In some embodiments, the "comparable subject" may be the subject being compared at a different time, e.g., the subject being treated (e.g., by administrating a combination of probenecid and/or valproic acid) may be subjected to conditions (e.g., administration of probenecid without valproic acid) as a "comparable subject" prior to the treatment. In some embodiments, the "comparable subject" may be the subject being compared at a different time, e.g., the subject being treated (e.g., by administrating a combination of valproic acid and/or a β-lactam compound) may be subjected to conditions (e.g., administration of valproic acid without a β-lactam compound) as a "comparable subject" prior to the treatment. In some embodiments, the "comparable subject" may be the subject being compared at a different time, e.g., the subject being treated (e.g., by administrating a combination of valproic acid and/or probenecid) may be subjected to conditions (e.g., administration of valproic acid without probenecid) as a "comparable subject" prior to the treatment.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

As used herein, the term "temporal proximity" refers to that administration of one therapeutic agent (e.g., a β-lactam, probenecid, or valproic acid compound disclosed herein) occurs within a time period before or after the administration of another therapeutic agent (e.g., a β-lactam, probenecid, or valproic acid), such that the therapeutic effect of the one therapeutic agent overlaps with the therapeutic effect of the other therapeutic agent. In some embodiments, the therapeutic effect of the one therapeutic agent completely overlaps with the therapeutic effect of the other therapeutic agent. In some embodiments, "temporal proximity" means that administration of one therapeutic agent occurs within a time period before or after the administration of another therapeutic agent, such that there is a synergistic effect between the one therapeutic agent and the other therapeutic agent. "Temporal proximity" may vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one therapeutic agent can occur in temporal proximity to a single administration of another therapeutic agent. In some embodiments, temporal proximity may change during a treatment cycle or within a dosing regimen.

It is to be understood that a compound of the present disclosure, or a pharmaceutically acceptable salt, polymorph or solvate thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

It is to be understood that one skilled in the art may refer to general reference texts for detailed descriptions of known techniques discussed herein or equivalent techniques. These texts include Ausubel et al., Current Protocols in Molecular Biology, John Wiley and Sons, Inc. (2005); Sambrook et al., Molecular Cloning, A Laboratory Manual ($3^{rd}$ edition), Cold Spring Harbor Press, Cold Spring Harbor, New York (2000); Coligan et al., Current Protocols in Immunology, John Wiley & Sons, N.Y.; Enna et al., Current Protocols in Pharmacology, John Wiley & Sons, N.Y.; Fingl et al., The Pharmacological Basis of Therapeutics (1975), Remington's Pharmaceutical Sciences, Mack Publishing Co., Easton, PA, $18^{th}$ edition (1990), Mandell, et al., Principles and Practice of Infectious Diseases, Saunders Publishing (8th edition, 2014). These texts can, of course, also be referred to in making or using an aspect of the disclosure.

It is to be understood that the present disclosure also provides pharmaceutical compositions comprising any compound described herein in combination with at least one pharmaceutically acceptable excipient or carrier.

As used herein, the term "pharmaceutical composition" is a formulation containing the compounds of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

It is to be understood that a pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods currently used for chemotherapeutic treatment. For example, a compound of the disclosure may be injected into the blood stream or body cavities or taken orally or applied through the skin with patches. The dose chosen should be sufficient to constitute effective treatment but not so high as to cause unacceptable side effects. The state of the disease condition and the health of the patient should preferably be closely monitored during and for a reasonable period after treatment.

As used herein, the term "therapeutically effective amount", refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

It is to be understood that, for any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the symptoms of the disease and also preferably causing complete regression of the disease. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in m², and age in years). An effective amount of a pharmaceutical agent is that which provides an objectively identifiable improvement as noted by the clinician or other qualified observer. Improvement in survival and growth indicates regression. As used herein, the term "dosage effective manner" refers to amount of an active compound to produce the desired biological effect in a subject or cell.

It is to be understood that the pharmaceutical compositions can be included in a container, pack, or dispenser together with instructions for administration.

It is to be understood that, for the compounds of the present disclosure being capable of further forming salts, all of these forms are also contemplated within the scope of the claimed disclosure.

As used herein, the term "pharmaceutically acceptable salts" refer to derivatives of the compounds of the present disclosure wherein the parent compound is modified by making acid or base salts thereof. In some embodiments, the pharmaceutically acceptable salt of a compound (e.g., a β-lactam compound or probenecid described herein) is also a prodrug of the compound. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3.

It is to be understood that all references to pharmaceutically acceptable salts include solvent addition forms (solvates) or crystal forms (polymorphs) as defined herein, of the same salt.

As used herein, the term "prodrug" refers to any agent which, when administered to a mammal, is converted in whole or in part to a targeted compound (e.g., a β-lactam compound or probenecid described herein). In some embodiments, the prodrug of a compound (e.g., a β-lactam compound or probenecid described herein) is also a pharmaceutically acceptable salt of the compound.

It is to be understood that the compounds of the present disclosure can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the disclosure can be found in *Remington: the Science and Practice of Pharmacy*, 19$^{th}$ edition, Mack Publishing Co., Easton, PA (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic schemes described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Figure 2:
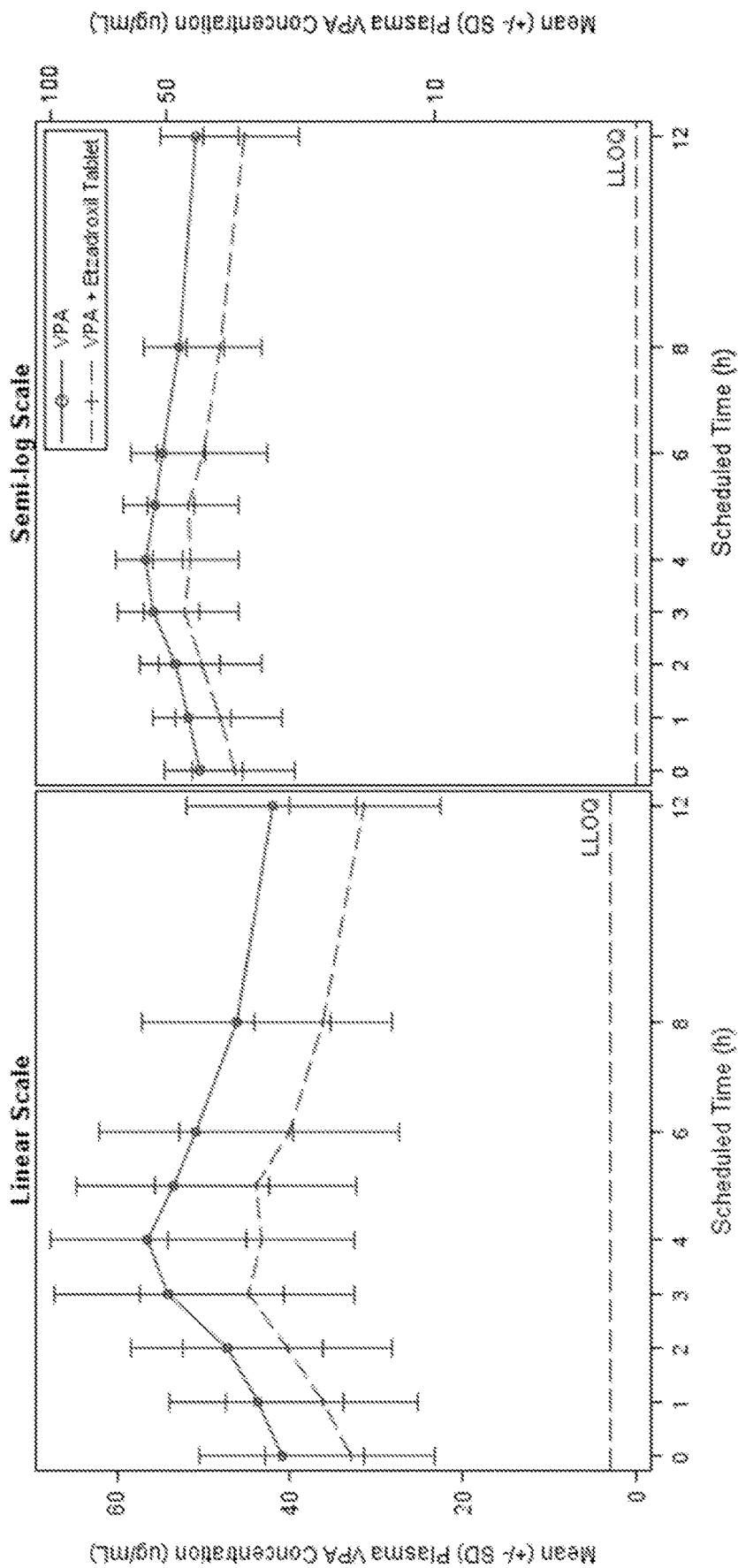
FIG. 2 is a diagram showing the mean (±standard deviation) plasma concentration of valproic acid (µg/ml) when being administered alone and in combination with sulopenem (in oral formulation).

Example 1. Effect of Sulopenem and Sulopenem Etzadroxil to Administration of Valproic Acid For Cohort 1, multiple doses of intravenous sulopenem (1,000 mg infused over 3 h) decreased area under the plasma concentration-time curve from time 0 extrapolated to the dosing interval ($AUC_{0-tau}$) for valproic acid and maximum observed plasma concentration during a dosing interval ($C_{maxSS}$) by approximately 33% and 28%, respectively, relative to administration of valproic acid alone. Concomitant administration of valproic acid and sulopenem etzadroxil (500 mg) without probenecid reduced valproic acid $AUC_{0-tau}$ and $C_{maxSS}$ approximately by 25% and 19%, respectively, relative to administration of valproic acid alone (Tables 1-3 and FIGS. 1-2). In contrast, the 90% confidence interval (CI) of the valproic acid and bilayer tablet to valproic acid alone geometric mean ratio (GMR) for $AUC_{0-tau}$ and $C_{maxSS}$ were within the 80 to 125% standard utilized to demonstrate bioequivalence.

TABLE 1

| | Sulopenem (intravenous, 1,000 mg/3 h) + Valproic Acid | Sulopenem etzadroxil (oral, 500 mg) + Valproic Acid |
|---|---|---|
| Change in VPA $AUC_{0-tau}$ relative to administration of VPA alone | −33% | −25% |
| Change in VPA $C_{maxSS}$ relative to administration of VPA alone | −28% | −19% |

TABLE 2

| PK Parameter (Unit) | Study Period 1 VPA | | Study Period 2 VPA + Etzadroxil Tablet | | Ratio Geometric LS Mean ([VPA + Etzadroxil Tablet]/ VPA) (%) | 90% CI for Ratio (%) [2] |
|---|---|---|---|---|---|---|
| | n | GM [1] | n | GM [1] | | |
| $AUC_{0-t}$ (h·µg/mL) | 10 | 559.30 | 10 | 442.41 | 79.1 | (74.13, 84.41) |
| $AUC_{0-tau}$ (h·µg/mL) | 6 | 540.77 | 6 | 405.87 | 75.1 | (69.00, 81.64) |
| $C_{maxSS}$ (µg/mL) | 10 | 57.74 | 10 | 46.69 | 80.9 | (75.24, 86.89) |
| Swing | 10 | 0.48 | 10 | 0.56 | 115.4 | (103.92, 128.10) |
| DOF | 6 | 0.42 | 6 | 0.48 | 113.9 | (98.36, 131.91) |

Note:
Cohort 3 = VPA versus VPA + etzadroxil tablet. Valproic acid alone is the reference group and VPA + etzadroxil tablet is the test group.
Note:
A paired t-test was performed on logarithm-transformed PK parameters. A subject must have had a calculable PK parameter in both treatments (test and reference) in order to be included in the analysis of that parameter.
[1] Geometric means are the means after back transformation to the original scale.
[2] The CIs are presented after back transformation to the original scale.
AUC = area under the plasma concentration-time curve; $AUC_{0-t}$ = AUC from time 0 to time of the last quantifiable concentration; $AUC_{0-tau}$ = AUC from time 0 extrapolated to the dosing interval, Tau; $C_{maxSS}$ = maximum observed plasma concentration during a dosing interval; CI = confidence interval; DOF = degree of fluctuation; etzadroxil tablet = sulopenem etzadroxil 500 mg tablet; GM = geometric mean; LS = least squares; PK = pharmacokinetic; VPA = valproic acid.

TABLE 3

| PK Parameter (Unit) | Study Period 1 VPA | | Study Period 2 1.0 g IV Sulopenem | | Ratio Geometric LS Mean ([VPA + IV Sulopenem]/ VPA) (%) | 90% CI for Ratio (%) [2] |
|---|---|---|---|---|---|---|
| | n | GM [1] | n | GM [1] | | |
| $AUC_{0-t}$ (h·µg/mL) | 10 | 560.84 | 10 | 380.00 | 67.8 | (62.65, 73.28) |
| $AUC_{0-tau}$ (h·µg/mL) | 6 | 559.20 | 6 | 371.83 | 66.5 | (63.09, 70.08) |
| $C_{maxSS}$ (µg/mL) | 10 | 56.66 | 10 | 40.83 | 72.1 | (66.01, 78.67) |
| Swing | 10 | 0.46 | 10 | 0.65 | 143.5 | (115.18, 178.91) |
| DOF | 6 | 0.38 | 6 | 0.48 | 125.1 | (94.70, 165.22) |

Note:
Cohort 1 = VPA versus VPA + 1.0 g sulopenem IV. Valproic acid alone is the reference group and VPA + sulopenem IV is the test group.
Note:
A paired t-test was performed on logarithm-transformed PK parameters. A subject must have had a calculable PK parameter in both treatments (test and reference) in order to be included in the analysis of that parameter.
3. Geometric means are the means after back transformation to the original scale.
4. The CIs are presented after back transformation to the original scale.
AUC = area under the plasma concentration-time curve; $AUC_{0-t}$ = AUC from time 0 to time of the last quantifiable concentration; $AUC_{0-tau}$ = area under the plasma concentration-time curve from time 0 extrapolated to the dosing interval, Tau; $C_{max}$ = maximum observed plasma concentration; $C_{maxSS}$ = $C_{max}$ during a dosing interval; CI = confidence interval; DOF = degree of fluctuation; GM = geometric mean; IV = intravenous; LS = least squares; PK = pharmacokinetic; VPA = valproic acid.

Figure 3:
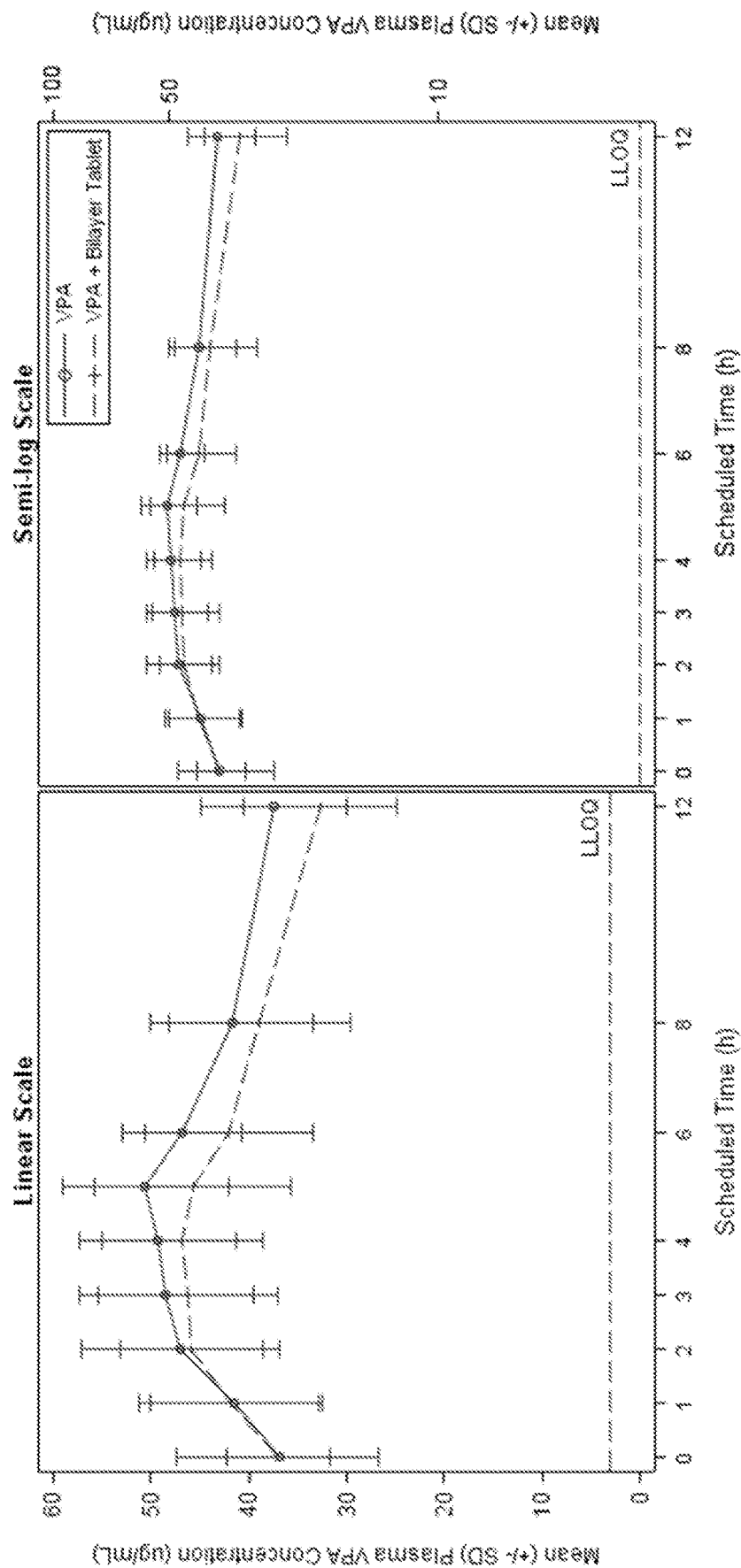
FIG. 3 is a diagram showing the mean (±standard deviation) plasma concentration of valproic acid (µg/ml) when being administered alone and in combination with sulopenem and probenecid (in oral formulation).

Example 2. Effect of Probenecid to Valproic Acid Bioavailability for Administration of Valproic Acid and Sulopenem Etzadroxil For Cohorts 2 and 3, all patients were administered valproic acid daily. Starting on the fifth day, Cohort 3 was administered the sulopenem etzadroxil tablet ("Etzadroxil Tablet") alone and Cohort 2 was administered the bilayer tablet of sulopenem etzadroxil and probenecid (500 mg sulopenem etzadroxil+500 mg probenecid film-coated bilayer tablet; "Bilayer Tablet"). The effects of the administration with respect to valproic acid bioavailability are shown in FIG. 3 and Tables 4-6. After one dose of oral administration sulopenem (bilayer or etzadroxil tablets), the median time to reach maximum observed plasma concentration ($t_{max}$) was 2.000 hours. The bilayer tablet of sulopenem etzadroxil/probenecid had no effect on the steady-state pharmacokinetic profile of valproic acid in healthy adult male subjects while multiple-dose intravenous sulopenem or sulopenem etzadroxil tablets had a weak effect. These findings confirm that the impact of probenecid on valproic acid bioavailability can occur as early as three days.

Overall, valproic acid and sulopenem were well tolerated and safe in all formulations. The most common drug-related treatment emergent adverse events (TEAEs) were diarrhea and urine odor abnormal, which were mild. There were no deaths or serious adverse events (SAEs). No clinically meaningful changes in vital signs, 12-lead ECGs, physical examinations, or clinical laboratory parameters were reported in the study.

TABLE 4

Summary of Pharmacokinetic Parameters for Valproic Acid.

| PK Parameter (Unit) | Study Period 1 VPA | | Study Period 2 VPA + Bilayer Tablet | | Ratio Geometric LS Mean ([VPA + Bilayer Tablet]/ VPA) (%) | 90% CI for Ratio (%) [2] |
|---|---|---|---|---|---|---|
| | n | GM [1] | n | GM [1] | | |
| $AUC_{0-t}$ (h·µg/mL) | 9 | 525.19 | 9 | 480.97 | 91.6 | (86.71, 96.72) |
| $AUC_{0-tau}$ (h·µg/mL) | 6 | 530.51 | 6 | 483.25 | 91.1 | (83.65, 99.19) |
| $C_{maxSS}$ (µg/mL) | 9 | 54.18 | 9 | 50.41 | 93.0 | (88.78, 97.50) |
| Swing | 9 | 0.49 | 9 | 0.56 | 114.1 | (88.37, 147.34) |
| DOF | 6 | 0.38 | 6 | 0.43 | 111.2 | (86.74, 142.64) |

Note:
Cohort 2 = VPA versus VPA + bilayer tablet. Valproic acid alone is the reference group and VPA + bilayer tablet is the test group.
Note:
A paired t-test was performed on logarithm-transformed PK parameters. A subject must have had a calculable PK parameter in both treatments (test and reference) in order to be included in the analysis of that parameter.
5. Geometric means are the means after back transformation to the original scale.
6. The CIs are presented after back transformation to the original scale.
AUC = area under the plasma concentration-time curve; $AUC_{0-t}$ = AUC from time 0 to time of the last quantifiable concentration; $AUC_{0-tau}$ = AUC from time 0 extrapolated to the dosing interval, Tau; bilayer tablet = sulopenem etzadroxil 500 mg + probenecid 500 mg film-coated, fixed-dose combination, bilayer tablet; CI = confidence interval; $C_{max}$ = maximum observed plasma concentration; $C_{maxSS}$ = maximum observed plasma concentration during a dosing interval; DOF = degree of fluctuation; GM = geometric mean; LS = least squares; PK = pharmacokinetic; VPA = valproic acid.

TABLE 5

Summary of Pharmacokinetic Parameters for Valproic Acid (ng/ml) by Treatment for Cohort 2 for Day 5 - Pharmacokinetic Parameter Population.

| PK Parameter (Unit) Statistic | Study Period 1 VPA | Study Period 2 VPA + Bilayer Tablet |
|---|---|---|
| | $C_{maxSS}$ (µg/mL) | |
| n | 10 | 9 |
| Mean (SD) | 54.15 (8.312) | 51.06 (8.219) |
| GM (CV %) | 53.59 (15.3) | 50.41 (17.5) |

TABLE 5-continued

Summary of Pharmacokinetic Parameters for Valproic Acid (ng/ml) by Treatment for Cohort 2 for Day 5 - Pharmacokinetic Parameter Population.

| PK Parameter (Unit) Statistic | Study Period 1 VPA | Study Period 2 VPA + Bilayer Tablet |
|---|---|---|
| $C_{minSS}$ (µg/mL) | | |
| n | 10 | 9 |
| Mean (SD) | 35.57 (6.321) | 32.63 (7.865) |
| GM (CV %) | 35.05 (18.4) | 31.79 (24.9) |
| $C_{avgSS}$ (h) | | |
| n | 7 | 9 |
| Mean (SD) | 43.51 (5.738) | 40.81 (8.068) |
| GM (CV %) | 43.16 (14.1) | 40.08 (20.5) |
| $t_{max}$ (h) | | |
| n | 10 | 9 |
| Median (min, max) | 4.000 (1.00, 6.00) | 3.000 (1.00, 5.00) |
| $AUC_{0-t}$ (h · µg/mL) | | |
| n | 10 | 9 |
| Mean (SD) | 522.11 (78.928) | 489.67 (96.811) |
| GM (CV %) | 516.69 (15.4) | 480.97 (20.5) |
| $AUC_{0-tau}$ (h · µg/mL) | | |
| n | 7 | 9 |
| Mean (SD) | 522.17 (68.854) | 489.67 (96.811) |
| GM (CV %) | 517.95 (14.1) | 480.97 (20.5) |
| $CL_{SS}/F$ (L/h) | | |
| n | 7 | 9 |
| Mean (SD) | 0.487 (0.0725) | 0.530 (0.1099) |
| $V_{zSS}/F$ (L) | | |
| n | 7 | 8 |
| Mean (SD) | 14.448 (3.3816) | 13.545 (7.2450) |
| DOF | | |
| n | 7 | 9 |
| Mean (SD) | 0.421 (0.1264) | 0.468 (0.1686) |
| Swing | | |
| n | 10 | 9 |
| Mean (SD) | 0.537 (0.1711) | 0.604 (0.2716) |
| $t_{last}$ (h) | | |
| n | 10 | 9 |
| Mean (SD) | 11.920 (0.0000) | 12.000 (0.0000) |

Note:
Cohort 2 = VPA versus VPA + bilayer tablet.

Note:
GM CV % = 100 × $(\exp(SD^2) - 1)^{0.5}$, where SD was the SD of the logarithm-transformed data.
$AUC_{0-t}$ = area under the plasma concentration-time curve from time 0 to time of the last quantifiable concentration;
$AUC_{0-tau}$ = area under the plasma concentration-time curve from time 0 extrapolated to the dosing interval, Tau;
bilayer tablet = sulopenem etzadroxil 500 mg + probenecid 500 mg film-coated, fixed-dose combination, bilayer tablet;
$C_{avgSS}$ = average plasma concentration at steady state;
$CL_{SS}/F$ = apparent total body clearance at steady state for oral administration;
$C_{maxSS}$ = maximum observed plasma concentration during a dosing interval;
$C_{minSS}$ = minimum observed plasma concentration during a dosing interval;
CV = coefficient of variation;
DOF = degree of fluctuation;
GM = geometric mean;
max = maximum;
min = minimum;
PK = pharmacokinetic;
SD = standard deviation;
$t_{last}$ = time to last measurable concentration;
$t_{max}$ = time to reach maximum observed plasma concentration;
VPA = valproic acid;
$V_{zSS}/F$ = apparent volume of distribution at steady state following oral administration.

TABLE 6

Summary of Pharmacokinetic Parameters for Plasma Valproic Acid (µg/mL) by Treatment for Cohort 3 - Pharmacokinetic Parameter Population

| PK Parameter (Unit) Statistic | Study Period 1 VPA | Study Period 2 VPA + Etzadroxil Tablet |
|---|---|---|
| $C_{maxSS}$ (µg/mL) | | |
| n | 10 | 10 |
| Mean (SD) | 58.64 (10.929) | 47.88 (11.073) |
| GM (CV %) | 57.74 (18.6) | 46.69 (24.4) |
| $C_{minSS}$ (µg/mL) | | |
| n | 10 | 10 |
| Mean (SD) | 39.51 (9.477) | 30.79 (8.951) |
| GM (CV %) | 38.47 (24.8) | 29.61 (30.6) |
| $C_{avgSS}$ (h) | | |
| n | 6 | 10 |
| Mean (SD) | 46.23 (11.734) | 38.03 (9.899) |
| GM (CV %) | 45.06 (24.7) | 36.88 (26.8) |
| $t_{max}$ (h) | | |
| n | 10 | 10 |
| Median (min, max) | 4.000 (2.00, 5.00) | 3.000 (2.00, 5.00) |
| $AUC_{0-t}$ (h · µg/mL) | | |
| n | 10 | 10 |
| Mean (SD) | 570.83 (122.096) | 456.27 (118.654) |
| GM (CV %) | 559.30 (21.5) | 442.41 (26.8) |
| $AUC_{0-tau}$ (h · µg/mL) | | |
| n | 6 | 10 |
| Mean (SD) | 554.71 (140.804) | 456.39 (118.791) |
| GM (CV %) | 540.77 (24.7) | 442.50 (26.8) |
| $CL_{SS}/F$ (L/h) | | |
| n | 6 | 10 |
| Mean (SD) | 0.473 (0.1086) | 0.583 (0.1551) |
| $V_{zSS}/F$ (L) | | |
| n | 6 | 7 |
| Mean (SD) | 13.835 (5.2162) | 14.154 (4.2502) |
| DOF | | |
| n | 6 | 10 |
| Mean (SD) | 0.432 (0.1131) | 0.463 (0.1223) |
| Swing | | |
| n | 10 | 10 |
| Mean (SD) | 0.509 (0.1663) | 0.587 (0.1900) |
| $t_{last}$ (h) | | |
| n | 10 | 10 |
| Mean (SD) | 11.920 (0.0000) | 11.997 (0.0095) |

Note:
Cohort 2 = VPA versus VPA + bilayer tablet.

Note:
GM CV % = 100 × $(\exp(SD^2) - 1)^{0.5}$, where SD was the SD of the logarithm-transformed data.
$AUC_{0-t}$ = area under the plasma concentration-time curve from time 0 to time of the last quantifiable concentration;
$AUC_{0-tau}$ = area under the plasma concentration-time curve from time 0 extrapolated to the dosing interval, Tau;
bilayer tablet = sulopenem etzadroxil 500 mg + probenecid 500 mg film-coated, fixed-dose combination, bilayer tablet;
$C_{avgSS}$ = average plasma concentration at steady state;
$CL_{SS}/F$ = apparent total body clearance at steady state for oral administration;
$C_{maxSS}$ = maximum observed plasma concentration during a dosing interval;
$C_{minSS}$ = minimum observed plasma concentration during a dosing interval;
CV = coefficient of variation;
DOF = degree of fluctuation;
GM = geometric mean;
max = maximum;
min = minimum;
PK = pharmacokinetic;
SD = standard deviation;
$t_{last}$ = time to last measurable concentration;
$t_{max}$ = time to reach maximum observed plasma concentration;
VPA = valproic acid;

TABLE 6-continued

Summary of Pharmacokinetic Parameters for
Plasma Valproic Acid (μg/mL) by Treatment
for Cohort 3 - Pharmacokinetic Parameter Population

| PK Parameter (Unit) Statistic | Study Period 1 VPA | Study Period 2 VPA + Etzadroxil Tablet |
|---|---|---|

$V_{zSS}/F$ = apparent volume of distribution at steady state following oral administration.

Example 3. Effect of Probenecid to Sulopenem Bioavailability for Administration of Valproic Acid and Sulopenem Etzadroxil For Cohorts 2 and 3, all patients were administered valproic acid daily. Starting on the fifth day, Cohort 3 was administered the sulopenem etzadroxil tablet ("Etzadroxil Tablet") alone and Cohort 2 was administered the bilayer tablet of sulopenem etzadroxil and probenecid (500 mg sulopenem etzadroxil+500 mg probenecid film-coated bilayer tablet; "Bilayer Tablet"). The effects of the administration with respect to sulopenem bioavailability are shown in Tables 7-10. Comparison between Table 7 and Table 9 shows enhanced pharmokinetic parameters for sulopenem by administration of the Bilayer Tablet after 5 days. Comparison between Table 8 and Table 10 shows enhanced pharmokinetic parameters for sulopenem by administration of the Bilayer Tablet after 7 days.

TABLE 7

Summary of Pharmacokinetic Parameters for
Sulopenem (ng/ml) by Treatment for Cohort 2
for Day 5 - Pharmacokinetic Parameter Population.

| PK Parameter (Unit) Statistic | Cohort 2 VPA + Bilayer Tablet |
|---|---|
| $C_{max}$ (ng/ml) | |
| n | 9 |
| Mean (SD) | 2843.3 (1186.93) |
| GM (CV %) | 2659.1 (39.1) |
| $t_{1/2}$ (h) | |
| n | 9 |
| Mean (SD) | 1.137 (0.1917) |
| $t_{max}$ (h) | |
| n | 9 |
| Median (min, max) | 2.000 (1.00, 5.00) |
| $AUC_{0-t}$ (h · ng/ml) | |
| n | 9 |
| Mean (SD) | 7082.3 (2249.64) |
| GM (CV %) | 6828.5 (27.7) |
| $AUC_{0-\infty}$ (h · ng/ml) | |
| n | 9 |
| Mean (SD) | 7143.3 (2243.54) |
| GM (CV %) | 6892.4 (27.4) |
| $AUC_{extrap}$ (%) | |
| n | 9 |
| Mean (SD) | 0.926 (0.4559) |
| CL/F (L/h) | |
| n | 9 |
| Mean (SD) | 54.65 (12.400) |
| $V_z/F$ (L) | |
| n | 9 |
| Mean (SD) | 87.07 (14.046) |

TABLE 7-continued

Summary of Pharmacokinetic Parameters for
Sulopenem (ng/ml) by Treatment for Cohort 2
for Day 5 - Pharmacokinetic Parameter Population.

| PK Parameter (Unit) Statistic | Cohort 2 VPA + Bilayer Tablet |
|---|---|
| $T_{free} > MIC_{0.5}$ (h) | |
| n | 9 |
| Mean (SD) | 3.920 (0.7502) |

Note:
Cohort 2 = VPA versus VPA + bilayer tablet.

Note:
GM CV % = 100 × $(exp(SD^2) - 1)^{0.5}$, where SD was the SD of the logarithm-transformed data.
$AUC_{0-\infty}$ = area under the plasma concentration-time curve from time 0 extrapolated to infinity;
$AUC_{0-t}$ = area under the plasma concentration-time curve from time 0 to time of the last quantifiable concentration;
$AUC_{extrap}$ = percentage of the area under the plasma concentration-time curve from time 0 extrapolated to infinity that is due to the extrapolation beyond the time of last quantifiable concentration;
bilayer tablet = sulopenem etzadroxil 500 mg + probenecid 500 mg film-coated, fixed-dose combination, bilayer tablet;
CL/F = apparent clearance for oral administration
$C_{max}$ = maximum observed plasma concentration;
CV = coefficient of variation;
GM = geometric mean;
max = maximum;
min = minimum;
PK = pharmacokinetic;
SD = standard deviation;
$t_{1/2}$ = terminal elimination half-life;
$T_{free} > MIC_{0.5}$ = time above minimum inhibitory concentration of 0.5 μg/mL;
$t_{max}$ = time to reach maximum observed plasma concentration;
VPA = valproic acid;
$V_z/F$ = apparent volume of distribution for oral administration.

TABLE 8

Summary of Pharmacokinetic Parameters for
Sulopenem (ng/mL) by Treatment for Cohort 2
for Day 7 - Pharmacokinetic Parameter Population.

| PK Parameter (Unit) Statistic | Day 7: VPA + Bilayer Tablet |
|---|---|
| $C_{maxSS}$ (ng/ml) | |
| n | 9 |
| Mean (SD) | 2818.9 (715.57) |
| GM (CV %) | 2740.2 (25.6) |
| $C_{minSS}$ (ng/ml) | |
| n | 9 |
| Mean (SD) | 15.98 (8.866) |
| GM (CV %) | 14.31 (50.0) |
| $C_{avgSS}$ (h) | |
| n | 9 |
| Mean (SD) | 617.54 (175.489) |
| GM (CV %) | 597.92 (26.7) |
| $t_{max}$ (h) | |
| n | 9 |
| Median (min, max) | 2.000 (1.00, 5.00) |
| $AUC_{0-t}$ (h · ng/mL) | |
| n | 9 |
| Mean (SD) | 7367.7 (2121.42) |
| GM (CV %) | 7128.5 (27.0) |
| $AUC_{0-tau}$ (h · ng/ml) | |
| n | 9 |
| Mean (SD) | 7410.4 (2105.86) |
| GM (CV %) | 7175.0 (26.7) |

TABLE 8-continued

Summary of Pharmacokinetic Parameters for
Sulopenem (ng/mL) by Treatment for Cohort 2
for Day 7 - Pharmacokinetic Parameter Population.

| PK Parameter (Unit) Statistic | Day 7: VPA + Bilayer Tablet |
|---|---|
| $CL_{SS}/F$ (L/h) | |
| n | 9 |
| Mean (SD) | 52.50 (12.615) |
| $V_{zSS}/F$ (L) | |
| n | 9 |
| Mean (SD) | 88.89 (23.188) |
| $R_{Cmax}$ | |
| n | 9 |
| Mean (SD) | 1.051 (0.2126) |

Note:
Cohort 2 = VPA versus VPA + bilayer tablet.
Note:
GM CV % = 100 × $(exp(SD^2) - 1)^{0.5}$, where SD was the SD of the logarithm-transformed data.
$AUC_{0-t}$ = area under the plasma concentration-time curve from time 0 to time of the last quantifiable concentration;
$AUC_{0-tau}$ = area under the plasma concentration-time curve from time 0 extrapolated to the dosing interval, Tau;
bilayer tablet = sulopenem etzadroxil 500 mg + probenecid 500 mg film-coated, fixed-dose combination, bilayer tablet;
$C_{avgSS}$ = average plasma concentration at steady state;
$CL_{SS}/F$ = apparent total body clearance at steady state for oral administration
$C_{maxSS}$ = maximum observed plasma concentration during a dosing interval;
$C_{minSS}$ = minimum observed plasma concentration during a dosing interval;
CV = coefficient of variation;
GM = geometric mean;
max = maximum;
min = minimum;
PK = pharmacokinetic;
$R_{AUC0-12}$ = accumulation ratio based on the area under the plasma concentration-time curve from time 0 to 12 hours after first and last dose;
$R_{Cmax}$ = accumulation ratio based on maximum concentrations after the first and last dose;
SD = standard deviation;
$T_{free} > MIC_{0.5t}$ = time above minimum inhibitory concentration of 0.5 μg/mL;
$t_{max}$ = time to reach maximum observed plasma concentration;
VPA = valproic acid;
$V_{zSS}/F$ = apparent volume of distribution at steady state following oral administration.

TABLE 9

Summary of Pharmacokinetic Parameters for
Sulopenem (ng/mL) by Treatment for Cohort 3
for Day 5 - Pharmacokinetic Parameter Population.

| PK Parameter (Unit) Statistic | Cohort 3 VPA + Etzadroxil Tablet |
|---|---|
| $C_{max}$ (ng/ml) | |
| n | 10 |
| Mean (SD) | 1825.0 (534.36) |
| GM (CV %) | 1755.1 (30.4) |
| $t_{1/2}$ (h) | |
| n | 8 |
| Mean (SD) | 1.118 (0.4545) |
| $t_{max}$ (h) | |
| n | 10 |
| Median (min, max) | 2.000 (1.00, 4.00) |
| $AUC_{0-t}$ (h · ng/mL) | |
| n | 10 |
| Mean (SD) | 4418.6 (846.92) |
| GM (CV %) | 4348.5 (18.9) |
| $AUC_{0-\infty}$ (h · ng/mL) | |
| n | 8 |
| Mean (SD) | 4551.3 (859.31) |
| GM (CV %) | 4486.0 (18.0) |

TABLE 9-continued

Summary of Pharmacokinetic Parameters for
Sulopenem (ng/mL) by Treatment for Cohort 3
for Day 5 - Pharmacokinetic Parameter Population.

| PK Parameter (Unit) Statistic | Cohort 3 VPA + Etzadroxil Tablet |
|---|---|
| $AUC_{extrap}$ (%) | |
| n | 8 |
| Mean (SD) | 1.080 (0.7928) |
| CL/F (L/h) | |
| n | 8 |
| Mean (SD) | 82.68 (13.867) |
| $V_z/F$ (L) | |
| n | 8 |
| Mean (SD) | 134.87 (66.954) |
| $T_{free} > MIC_{0.5}$ (h) | |
| n | 10 |
| Mean (SD) | 3.134 (0.6581) |

Note:
Cohort 3 = VPA versus VPA + etzadroxil tablet.
Note:
GM CV % = 100 × $(exp(SD^2) - 1)^{0.5}$, where SD was the SD of the logarithm-transformed data.
$AUC_{0-\infty}$ = area under the plasma concentration-time curve from time 0 extrapolated to infinity;
$AUC_{0-t}$ = area under the plasma concentration-time curve from time 0 to time of the last quantifiable concentration;
$AUC_{extrap}$ = percentage of the area under the plasma concentration-time curve from time 0 extrapolated to infinity that is due to the extrapolation beyond the time of last quantifiable concentration;
CL/F = apparent clearance for oral administration;
$C_{max}$ = maximum observed plasmaconcentration;
CV = coefficient of variation;
etzadroxil tablet = sulopenem etzadroxil 500 mg tablet;
GM = geometric mean;
max = maximum;
min = minimum;
PK = pharmacokinetic;
SD = standard deviation;
$t_{1/2}$ = terminal elimination half-life;
$T_{free} > MIC_{0.5}$ = time above minimum inhibitory concentration;
$t_{max}$ = time to reach maximum observed plasma concentration;
VPA = valproic acid;
$V_z/F$ = apparent volume of distribution for oral administration.

TABLE 10

Summary of Pharmacokinetic Parameters for
Sulopenem (ng/mL) by Treatment for Cohort 3 for
Day 7 - Pharmacokinetic Parameter Population.

| PK Parameter (Unit) Statistic | Day 7: VPA + Etzadroxil Tablet |
|---|---|
| $C_{maxSS}$ (ng/ml) | |
| n | 10 |
| Mean (SD) | 1624.6 (360.40) |
| GM (CV %) | 1584.5 (24.8) |
| $C_{minSS}$ (ng/ml) | |
| n | 10 |
| Mean (SD) | 10.51 (1.613) |
| GM (CV %) | 10.42 (13.1) |
| $C_{avgSS}$ (h) | |
| n | 10 |
| Mean (SD) | 298.37 (54.739) |
| GM (CV %) | 294.15 (17.7) |
| $t_{max}$ (h) | |
| n | 10 |
| Median (min, max) | 2.000 (1.00, 3.00) |

TABLE 10-continued

Summary of Pharmacokinetic Parameters for
Sulopenem (ng/mL) by Treatment for Cohort 3 for
Day 7 - Pharmacokinetic Parameter Population.

| PK Parameter (Unit) Statistic | Day 7: VPA + Etzadroxil Tablet |
|---|---|
| $AUC_{0-t}$ (h · ng/ml) | |
| n | 10 |
| Mean (SD) | 3548.1 (667.45) |
| GM (CV %) | 3495.6 (18.1) |
| $AUC_{0-tau}$ (h · ng/ml) | |
| n | 10 |
| Mean (SD) | 3580.4 (656.86) |
| GM (CV %) | 3529.8 (17.7) |
| $CL_{SS}/F$ (L/h) | |
| n | 10 |
| Mean (SD) | 105.09 (17.590) |
| $V_{zSS}/F$ (L) | |
| n | 10 |
| Mean (SD) | 150.51 (41.602) |
| $R_{Cmax}$ | |
| n | 10 |
| Mean (SD) | 0.947 (0.3072) |
| $R_{AUC0-12}$ | |
| n | 8 |
| Mean (SD) | 0.798 (0.0952) |
| $T_{free} > MIC_{0.5}$ (h) | |
| n | 10 |
| Mean (SD) | 2.677 (0.5128) |

Note:
Cohort 3 = VPA versus VPA + etzadroxil tablet.
Note:
GM CV % = 100 × $(exp(SD^2) - 1)^{0.5}$, where SD was the SD of the logarithm-transformed data.
$AUC_{0-t}$ = area under the plasma concentration-time curve from time 0 to time of the last quantifiable concentration;
$AUC_{0-tau}$ = area under the plasma concentration-time curve from time 0 extrapolated to the dosing interval, Tau;
$C_{avgSS}$ = average plasma concentration at steady state;
$CL_{SS}/F$ = apparent total body clearance at steady state for oral administration
$C_{maxSS}$ = maximum observed plasma concentration during a dosing interval;
$C_{minSS}$ = minimum observed plasma concentration during a dosing interval;
CV = coefficient of variation;
etzadroxil tablet = sulopenem etzadroxil 500 mg tablet;
GM = geometric mean;
max = maximum;
min = minimum;
PK = pharmacokinetic;
$R_{AUC0-12}$ = accumulation ratio based on the area under the plasma concentration-time curve from time 0 to 12 hours after first and last dose;
$R_{Cmax}$ = accumulation ratio based on maximum concentrations after the first and last dose;
SD = standard deviation;
$T_{free} > MIC_{0.5}$ = time above minimum inhibitory concentration;
$t_{max}$ = time to reach maximum observed plasma concentration;
VPA = valproic acid;
$V_{zSS}/F$ = apparent volume of distribution at steady state following oral administration.

EQUIVALENTS

It is to be understood that the invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of treating a disease being an uncomplicated urinary tract infection, a complicated urinary tract infection, a complicated intra-abdominal infection, an uncomplicated intra-abdominal infection, pneumonia, otitis media, sinusitis, gonococcal urethritis, pelvic inflammatory disease, prostatitis, bone infection, joint infection, diabetic foot infection, or infectious diarrhea, comprising administering to a subject in need thereof:
a pharmaceutically effective amount of valproic acid or a pharmaceutically acceptable salt thereof;
a pharmaceutically effective amount of a β-lactam compound or a pharmaceutically acceptable salt thereof, and
a pharmaceutically effective amount of probenecid or a pharmaceutically acceptable salt thereof,
wherein the β-lactam compound is

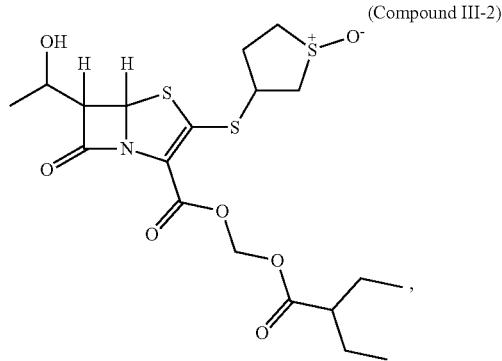

(Compound III-2)

or a pharmaceutically acceptable salt thereof.

2. The method of claim 1, wherein the administration reduces or alleviates a side effect.

3. The method of claim 1, wherein the side effect is mania, a seizure, an increased seizure potential, a reduced concentration of valproic acid in the subject, neuromotor impairment, a potential for neuromotor impairment, or a reduced concentration of valproic acid in the subject associated with the co-administration of a β-lactam compound.

4. The method of claim 1, wherein the administration results in a plasma concentration for the valproic acid or pharmaceutically acceptable salt thereof having a maximum plasma concentration ($C_{max}$) that is higher in the subject in need thereof as compared to a comparable subject being administered with the β-lactam compound or pharmaceutically acceptable salt thereof and valproic acid or pharmaceutically acceptable salt thereof without probenecid or pharmaceutically acceptable salt thereof within about 15 minutes, about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration.

5. The method of claim 1, wherein the administration results in a plasma concentration for valproic acid or pharmaceutically acceptable salt thereof having an area under the curve (AUC) in the subject in need thereof that is substantially the same as compared to a comparable subject being administered with valproic acid or pharmaceutically acceptable salt thereof without the β-lactam compound, probenecid, or the pharmaceutically acceptable salt thereof within about 15 minutes, about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration.

6. The method of claim 1, wherein the subject in need thereof is a human.

7. The method of claim 1, wherein the β-lactam compound is selected from

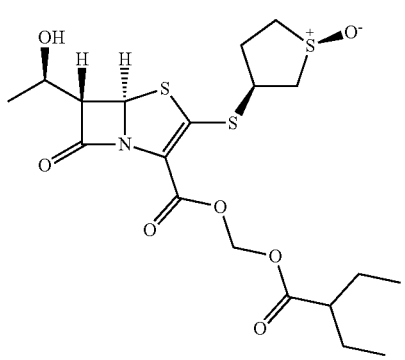

(Compound III-2b)

and pharmaceutically acceptable salts thereof.

8. The method of claim 1, wherein the pharmaceutical salt of valproic acid is a sodium salt, a potassium salt, a lithium salt, an ammonium salt, a calcium salt, a magnesium salt, an iron salt, a zinc salt, a copper salt, a manganese salt, or an aluminum salt.

9. The method of claim 1, wherein valproic acid or the pharmaceutically acceptable salt thereof is administered once daily, twice daily, or three or more times daily.

10. The method of claim 1, wherein valproic acid or the pharmaceutically acceptable salt thereof is administered by an oral administration.

11. The method of claim 1, wherein valproic acid or the pharmaceutically acceptable salt thereof, the β-lactam compound or the pharmaceutically acceptable salt thereof, and probenecid or the pharmaceutically acceptable salt thereof are administered orally.

12. The method of claim 1, wherein a bilayer tablet comprising the β-lactam compound or the pharmaceutically acceptable salt thereof and probenecid or the pharmaceutically acceptable salt thereof is administered, wherein the bilayer tablet comprises:
a second layer comprising the β-lactam compound or the pharmaceutically acceptable salt thereof; and
a first layer comprising probenecid or the pharmaceutically acceptable salt thereof.

13. The method of claim 12, wherein the first layer comprises from 20 mg to about 5 g, from about 50 mg to about 2 g, from about 80 mg to about 1 g, from about 100 mg to about 900 mg, from about 200 mg to about 800 mg, from about 300 mg to about 700 mg, from about 400 mg to about 600 mg, from about 450 mg to about 550 mg, or from about 480 mg to about 520 mg of probenecid or the pharmaceutically acceptable salt thereof, and
the second layer comprises from 20 mg to about 5 g, from about 50 mg to about 2 g, from about 80 mg to about 1 g, from about 100 mg to about 900 mg, from about 200 mg to about 800 mg, from about 300 mg to about 700 mg, from about 400 mg to about 600 mg, from about 450 mg to about 550 mg, or from about 480 mg to about 520 mg of the β-lactam compound or the pharmaceutically acceptable salt thereof.

14. The method of claim 12, wherein the bilayer tablet further comprises one or more of pharmaceutical excipients, wherein the one or more of pharmaceutical excipients are selected from cellulose, sodium croscamellose, magnesium stearate, lactose monohydrate, and hydroxypropylcellulose.

15. The method of claim 1, wherein the valproic acid or the pharmaceutically acceptable salt thereof is administered at a dosage of about 50 mg per day, about 100 mg per day, about 150 mg per day, about 200 mg per day, about 250 mg per day, about 300 mg per day, about 350 mg per day, about 400 mg per day, about 500 mg per day, about 1 g per day, about 2 g per day, about 3 g per day, about 4 g per day, or about 5 g per day.

16. The method of claim 1, wherein:
the valproic acid or the pharmaceutically acceptable salt thereof is administered at a dosage of 500±300 mg per day, 500±250 mg per day, 500±200 mg per day, 500±150 mg per day, 500±100 mg per day, 500±90 mg per day, 500±80 mg per day, 500±70 mg per day, 500±60 mg per day, 500±50 mg per day, 500±40 mg per day, 500±30 mg per day, 500±20 mg per day, 500±10 mg per day, 500±5 mg per day, 500±4 mg per day, 500±3 mg per day, 500±2 mg per day, 500±1 mg per day;
the β-lactam compound or the pharmaceutically acceptable salt thereof is administered at a dosage of 500±300 mg per day, 500±250 mg per day, 500±200 mg per day, 500±150 mg per day, 500±100 mg per day, 500±90 mg per day, 500±80 mg per day, 500±70 mg per day, 500±60 mg per day, 500±50 mg per day, 500±40 mg per day, 500±30 mg per day, 500±20 mg per day, 500±10 mg per day, 500±5 mg per day, 500±4 mg per day, 500±3 mg per day, 500±2 mg per day, 500±1 mg per day; and
the probenecid or the pharmaceutically acceptable salt thereof is administered at a dosage of 500±300 mg per day, 500±250 mg per day, 500±200 mg per day, 500±150 mg per day, 500±100 mg per day, 500±90 mg per day, 500±80 mg per day, 500±70 mg per day, 500±60 mg per day, 500±50 mg per day, 500±40 mg per day, 500±30 mg per day, 500±20 mg per day, 500±10 mg per day, 500±5 mg per day, 500±4 mg per day, 500±3 mg per day, 500±2 mg per day, 500±1 mg per day.

* * * * *